US012708745B2

(12) United States Patent
Lopez et al.

(10) Patent No.: US 12,708,745 B2
(45) Date of Patent: Aug. 18, 2026

(54) FLARED INSERT MEMBER FOR USE WITH CATHETER ASSEMBLY

(71) Applicant: Biosense Webster (Israel) Ltd., Yokneam (IL)

(72) Inventors: Simon P. Lopez, Fontana, CA (US); Cesar Fuentes-Ortega, Pasadena, CA (US); Pieter E. Van Niekerk, Monrovia, CA (US); Raymond Yue-sing Tang, Rosemead, CA (US); Sean D. Thaler, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1058 days.

(21) Appl. No.: 17/018,104

(22) Filed: Sep. 11, 2020

(65) Prior Publication Data

US 2021/0113812 A1 Apr. 22, 2021

Related U.S. Application Data

(60) Provisional application No. 62/924,443, filed on Oct. 22, 2019.

(51) Int. Cl.
*A61M 25/01* (2006.01)
*A61B 5/00* (2006.01)
(Continued)

(52) U.S. Cl.
CPC ......... *A61M 25/0105* (2013.01); *A61B 5/283* (2021.01); *A61B 5/6852* (2013.01);
(Continued)

(58) Field of Classification Search
CPC .. A61M 2025/0681; A61M 2025/0293; A61M 2025/0675; A61M 2025/1081;
(Continued)

(56) References Cited

U.S. PATENT DOCUMENTS 4,515,583 A * 5/1985 Sorich ................ A61F 9/00745
604/239
5,738,096 A 4/1998 Ben-Haim
(Continued)

FOREIGN PATENT DOCUMENTS

WO 1998/039056 A2 9/1998

OTHER PUBLICATIONS

International Search Report and Written Opinion dated Feb. 2, 2021, for International Application No. PCT/IB2020/059670, 12 pages.
(Continued)

*Primary Examiner* — Laura A Bouchelle
*Assistant Examiner* — Sarah Dympna Grasmeder
(74) *Attorney, Agent, or Firm* — FBT Gibbons LLP

(57) ABSTRACT

An apparatus includes a cylindrical shaft and an outwardly flared feature. The cylindrical shaft is sized for insertion into an insertion port of a cardiovascular catheter guiding sheath. The cylindrical shaft includes a proximal end, a distal end, and a lumen extending from the proximal end to the distal end. The lumen is sized to receive an end effector and catheter of a cardiovascular catheter instrument. The outwardly flared feature is at the proximal end of the cylindrical shaft. The outwardly flared feature defines an angled surface leading into the lumen.

17 Claims, 21 Drawing Sheets

(51) Int. Cl.

| | |
|---|---|
| ***A61B 5/283*** | (2021.01) |
| ***A61B 18/14*** | (2006.01) |
| ***A61B 34/20*** | (2016.01) |
| *A61B 17/00* | (2006.01) |
| *A61B 18/00* | (2006.01) |

(52) U.S. Cl.

CPC .......... *A61B 18/1492* (2013.01); *A61B 34/20* (2016.02); *A61B 2017/00199* (2013.01); *A61B 2017/00327* (2013.01); *A61B 2018/00077* (2013.01); *A61B 2018/00351* (2013.01); *A61B 2018/00577* (2013.01); *A61B 2018/00821* (2013.01); *A61B 2034/2048* (2016.02); *A61B 2034/2051* (2016.02); *A61B 2034/2055* (2016.02); *A61B 2034/2063* (2016.02); *A61B 2218/002* (2013.01); *A61B 2562/0261* (2013.01); *A61B 2562/028* (2013.01)

(58) Field of Classification Search

CPC .. A61M 25/0662; A61M 25/02; A61M 25/01; A61M 25/0668; A61M 2039/0294; A61M 2039/062; A61M 2039/0633

See application file for complete search history.

(56) References Cited

U.S. PATENT DOCUMENTS

| | | | | |
|---|---|---|---|---|
| 5,997,562 | A * | 12/1999 | Zadno-Azizi | ..... A61M 25/0662 606/108 |
| 6,325,972 | B1 | 12/2001 | Jacobs et al. | |
| 6,365,102 | B1 | 4/2002 | Wu et al. | |
| 6,447,719 | B1 | 9/2002 | Agamohamadi et al. | |
| 6,846,443 | B1 | 1/2005 | Jackson et al. | |
| 6,852,277 | B2 | 2/2005 | Platt, Jr. et al. | |
| 6,852,279 | B2 | 2/2005 | Williams et al. | |
| 6,939,519 | B2 | 9/2005 | Agamohamadi et al. | |
| 8,956,353 | B2 | 2/2015 | Govari et al. | |
| 9,480,416 | B2 | 11/2016 | Govari et al. | |
| 9,801,585 | B2 | 10/2017 | Shah et al. | |
| 9,907,480 | B2 | 3/2018 | Basu et al. | |
| 10,130,422 | B2 | 11/2018 | Ditter | |
| 12,357,766 | B2 | 7/2025 | Zhang et al. | |
| 2001/0001128 | A1 | 5/2001 | Holman et al. | |
| 2004/0059291 | A1 | 3/2004 | McDonnell et al. | |
| 2011/0022075 | A1 | 1/2011 | Christiansen et al. | |
| 2011/0208129 | A1* | 8/2011 | Bonnette | ........... A61M 39/0613 604/247 |
| 2012/0296313 | A1* | 11/2012 | Andreacchi | ........... A61M 39/06 604/509 |
| 2013/0030426 | A1 | 1/2013 | Gallardo et al. | |
| 2015/0217092 | A1 | 8/2015 | Kokate et al. | |
| 2016/0220272 | A1* | 8/2016 | Blumenkranz | .... A61B 17/3462 |
| 2017/0252474 | A1 | 9/2017 | Thompson et al. | |
| 2017/0312022 | A1* | 11/2017 | Beeckler | ................ A61B 5/283 |
| 2018/0056038 | A1 | 3/2018 | Aujla | |
| 2018/0071017 | A1 | 3/2018 | Bar-tal et al. | |
| 2018/0236208 | A1* | 8/2018 | Pederson, Jr. | .......... A61F 2/962 |
| 2019/0224448 | A1 | 7/2019 | Connors et al. | |

OTHER PUBLICATIONS

Japanese First Office Action dated Mar. 19, 2024, for Application No. 2022-523623, 5 pages.

Chinese First Office Action and Search Report dated May 22, 2025, for Application No. 202080074108.9, 10 pages.

European Communication dated Mar. 3, 2025, for Application No. 20804334.9, 4 pages.

* cited by examiner

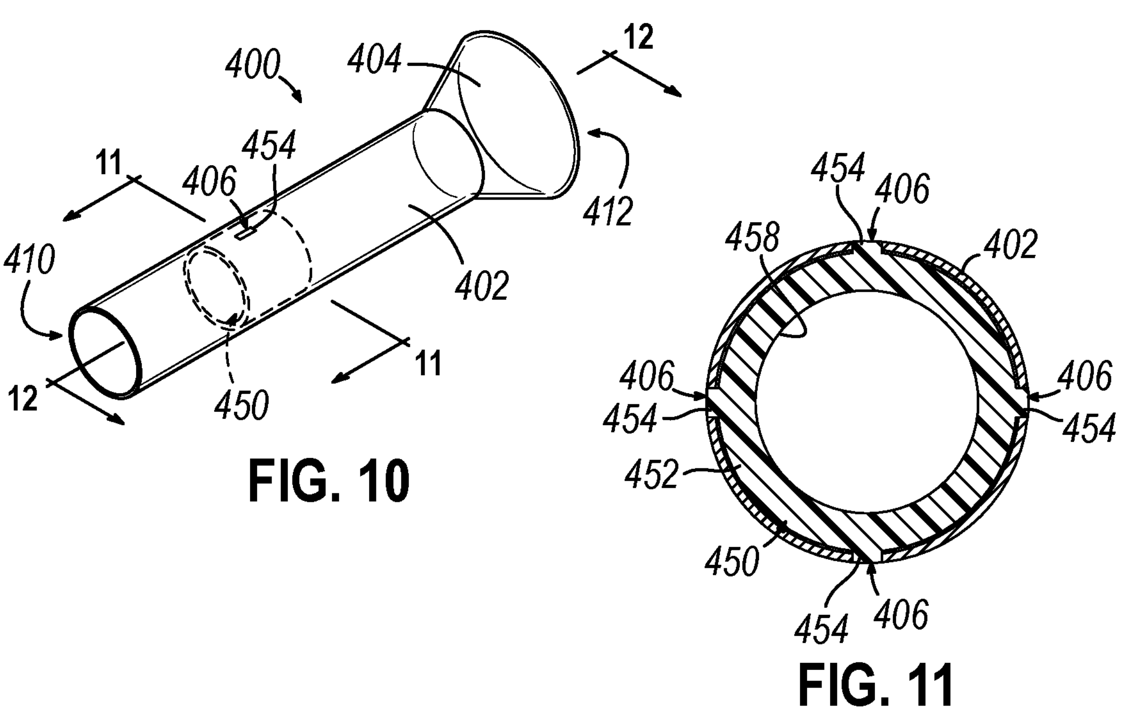
FIG. 10
FIG. 11
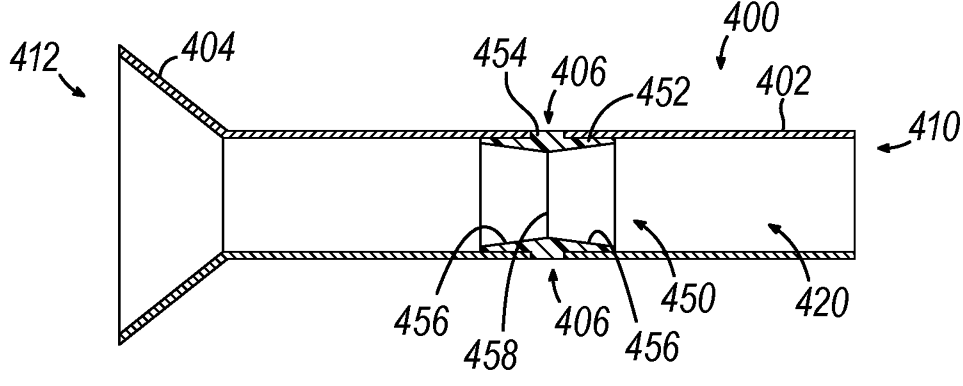
FIG. 12A
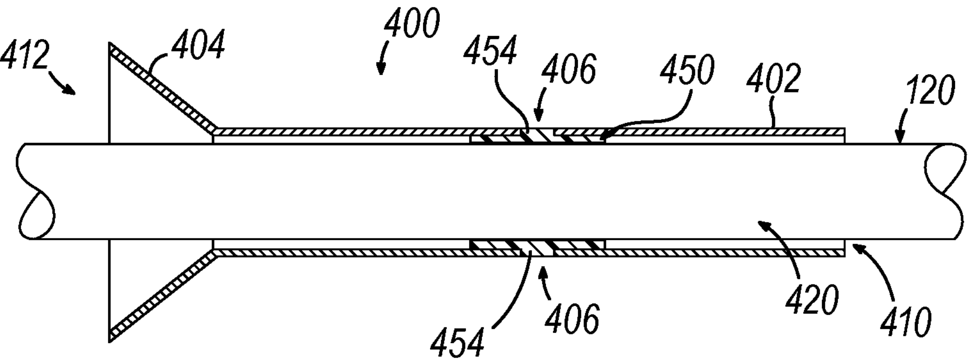
FIG. 12B 852
800
856
850
854
OD1

852
OD2
850
856
800
854

FLARED INSERT MEMBER FOR USE WITH CATHETER ASSEMBLY

PRIORITY

This application claims priority to U.S. Provisional Pat. App. No. 62/924,443, entitled "Flared Insert Member for Use with Catheter Assembly," filed Oct. 22, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

FIG. 10 depicts a perspective view of another example of an insert member that may be used with the catheter assembly of FIG. 1 and the guiding sheath of FIG. 4;

FIG. 11 depicts a cross-sectional view of the insert member of FIG. 10, taken along line 11-11 of FIG. 10;

FIG. 12A depicts a cross-sectional view of the insert member of FIG. 10, taken along line 12-12 of FIG. 10;

FIG. 12B depicts a cross-sectional view of the insert member of FIG. 10, taken along line 12-12 of FIG. 10, with the catheter of the catheter assembly of FIG. 1 disposed in the insert member;

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc.

should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. OVERVIEW OF EXAMPLE OF A CATHETER SYSTEM

Figure 1:
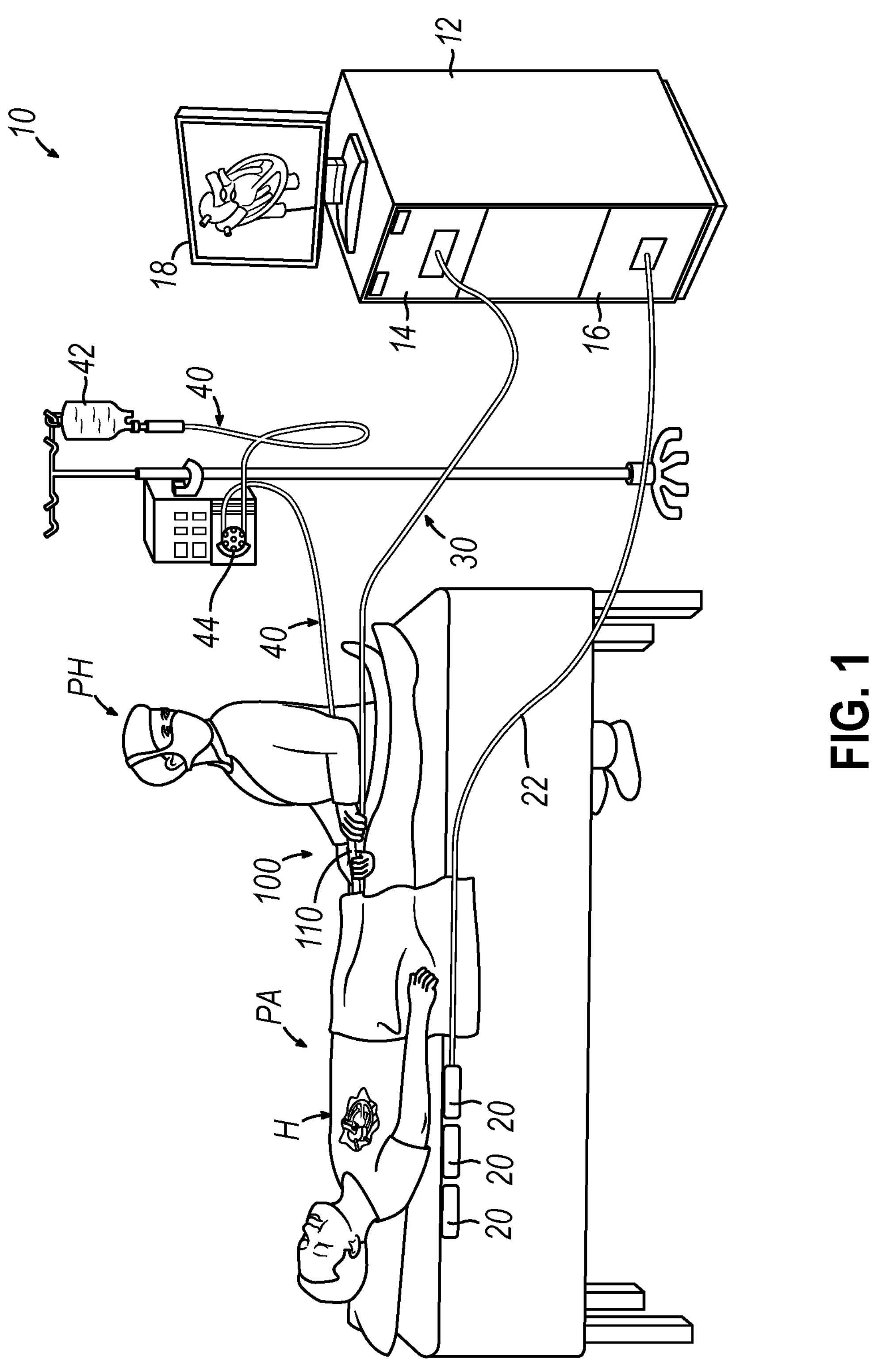
FIG. 1 depicts a schematic view of a medical procedure in which a catheter of a catheter assembly is inserted in a patient.
Figure 2:
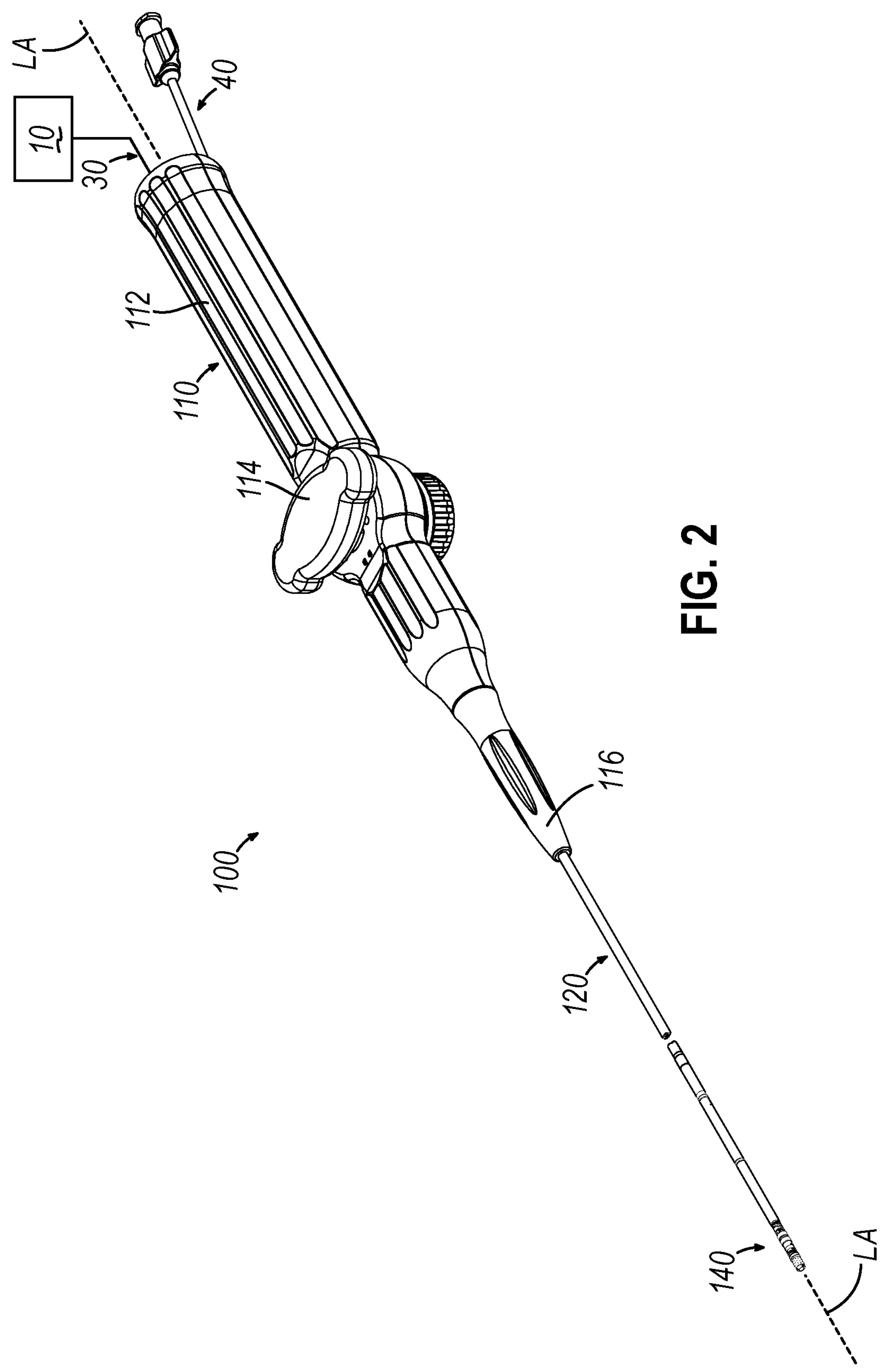
FIG. 2 depicts a perspective view of the catheter assembly of FIG. 1.

FIG. 1 shows an exemplary medical procedure and associated components of a cardiac catheter system that may be used to provide EP mapping or cardiac ablation as referred to above. In particular, FIG. 1 shows a physician (PH) grasping a handle assembly (110) of a catheter assembly (100), with an end effector (140) of a catheter (120) (shown in FIGS. 2-3 but not shown in FIG. 1) of catheter assembly (100) disposed in a patient (PA) to map potentials in tissue or ablate tissue in or near the heart (H) of the patient (PA). As shown in FIG. 2, catheter assembly (100) includes handle assembly (110), catheter (120) extending distally from handle assembly (110), end effector (140) located at a distal end of catheter (120), and a deflection drive actuator (114) associated with handle assembly (110).

As will be described in greater detail below, end effector (140) includes various components configured to deliver RF energy to targeted tissue sites, provide EP mapping functionality, track external forces imparted on end effector (140), track the location of end effector (140), or disperse irrigation fluid. Deflection drive actuator (114) is rotatable relative to a casing (112) of handle assembly (110) to thereby deflect end effector (140) and a distal portion of catheter (120) away from a central longitudinal axis (LA) defined by a proximal portion of catheter (120). Various suitable components that may be coupled with deflection drive actuator (114) and catheter (120) to provide such functionality will be apparent to those skilled in the art in view of the teachings herein.

Figure 3:
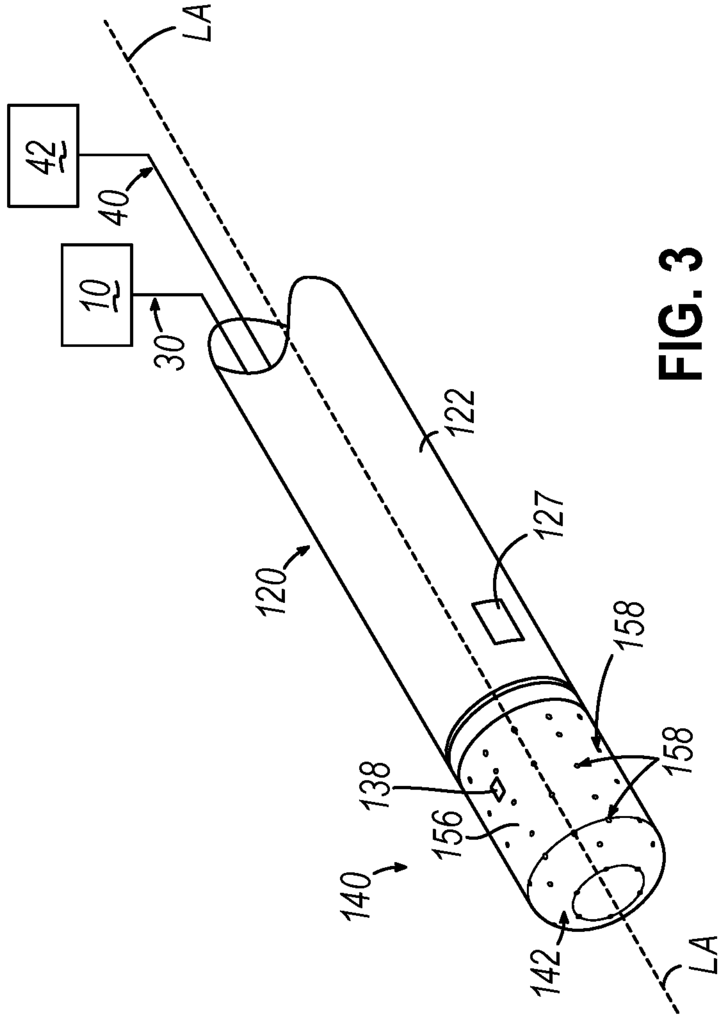
FIG. 3 depicts a perspective view of an end effector of the catheter assembly of FIG. 1.

As shown in FIG. 3, catheter (120) includes an elongate flexible shaft (122), with end effector (140) extending distally from shaft (122). The proximal end of catheter (120) extends distally from a nozzle member (116) of handle assembly (110). In some versions, a heat shrink wrap (not shown) is provided about catheter (120), at the junction of the proximal end of catheter (120) and nozzle member (116). End effector (140) at the distal end of catheter (120) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrode pairs (320) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly (127) in catheter (120) near end effector (140). In such versions, the processor of console (12) is also operable to process the position indicative signals from navigation sensor assembly (127) to thereby determine the position of end effector (140) within the patient (PA). In some versions, navigation sensor assembly (127) includes two or more coils that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. While navigation sensor assembly (127) is shown as being disposed in the distal end of catheter (120), navigation sensor assembly (127) may instead be positioned in end effector (140). Alternatively, catheter (120) and end effector (140) may lack a navigation sensor assembly (127).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from navigation sensor assembly (127) of end effector (140). For instance, as end effector (140) of catheter (120) moves within the patient (PA), the corresponding position data from navigation sensor assembly (127) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (140) on the images of the patient's anatomy, such as by superimposing an illuminated dot, a crosshair, a graphical representation of end effector (140), or some other form of visual indication. Such a superimposed visual indication may also move within the images of the patient anatomy on display (18) in real time as the physician moves end effector (140) within the patient (PA), thereby providing real-time visual feedback to the operator about the position of end effector (140) within the patient (PA) as end effector (140) moves within the patient (PA). The images provided through display (18) may thus effectively provide a video tracking the position of end effector (140) within a patient (PA), without necessarily having any optical instrumentation (i.e., cameras) viewing end effector (140). In the same view, display (18) may simultaneously visually indicate the locations of aberrant conductive tissue sites detected through EP mapping. The physician (PH) may thus view display (18) to observe the real time positioning of end effector (140) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. EXAMPLE OF AN END EFFECTOR

As mentioned above, end effector (140) includes various components configured to deliver RF energy to targeted tissue sites, provide EP mapping functionality, track external forces imparted on end effector (140), track the location of end effector (140) within the patient (PA), and emit irrigation fluid. As shown in FIG. 3, end effector (140) of the present example includes a distal tip member (142), which further includes a cylindraceous body (156) with a dome tip. Cylindraceous body (156) and the dome tip may be formed of an electrically conductive material, such as metal. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14). Distal tip member (142) may also include one or more thermocouples that are configured to provide temperature sensing capabilities. This may prevent overheating of distal tip member (142) or adjacent tissue.

As also shown in FIG. 3, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). EP mapping microelectrodes (138) may thus be used to determine locations of aberrant electrical activity in tissue within a cardiovascular anatomical structure (e.g., pulmonary vein, etc.). Signals picked up by EP mapping microelectrodes (138) may be communicated to first driver module (14) of console (12) via cable (30). First driver module (14) may process the EP mapping signals and provide the physician (PH) with corresponding feedback indicating the locations of aberrant electrical activity in accordance with the teachings of various references cited herein.

In versions where cylindraceous body (156) is formed of an electrically conductive material to provide RF electrical energy for tissue ablation, an electrically insulating material may be interposed between cylindraceous body (156) and EP mapping microelectrodes (138) to thereby electrically isolate EP mapping microelectrodes (138) from cylindraceous body (156). EP mapping microelectrodes (138) may be constructed and operable in accordance with the teachings of various patent references cited herein. While only one EP mapping microelectrode (138) is shown, distal tip member (142) may include two or more EP mapping microelectrodes (138). Alternatively, distal tip member (142) may lack EP mapping microelectrodes (138) altogether.

In some variations, end effector (140) may further include force sensor that is configured to sense external forces that impinge against distal tip member (142). By way of example only, such a force sensor may take the form of a strain gauge or any other suitable component(s). When distal tip (142) encounters external forces (e.g., when distal tip (142) is pressed against tissue), those external forces are communicated from distal tip (142) to the force sensor, such that the force sensor may generate a suitable signal corresponding to the magnitude and direction of the external force. The signals from the force sensor may be communicated to first driver module (14) of console (12) via cable (30). First driver module (14) may process the strain signals in accordance with any suitable fashion as would be apparent to one skilled in the art in view of the teachings herein. By way of example only, console (12) may provide audible feedback to alert the physician (PH) when the force sensor indicates that distal tip member (142) is encountering forces over a predetermined threshold, to thereby prevent the physician (PH) from unwittingly damaging a cardiovascular anatomical structure with distal tip member (142). In some versions, the force sensor may be omitted.

In addition to the foregoing, end effector (140) and other aspects of catheter assembly (100) may be configured and operable in accordance with at least some of the teachings of any one or more of the various patent documents that are incorporated by reference herein. Alternatively, end effector (140) may have any other suitable components, features, and capabilities.

III. EXAMPLE OF GUIDING SHEATH

In some procedures, the physician (PH) may wish to introduce catheter (120) into the patient (PA) via a guiding sheath. In some such procedures, the guiding sheath may be inserted into the patient (PA) (e.g., via the leg or groin of the patient (PA)); and then be advanced along a vein or artery to reach a position in or near the heart (H). Once the guiding sheath is suitably positioned in the patient (PA), the physician (PA) may then advance end effector (140) and catheter (120) into the guiding sheath until end effector (140) exits the distal end of the guiding sheath. The physician (PA) may then operate catheter assembly (100) to provide EP mapping, ablation, or any other kind of operations in or near the heart (H) of the patient (PA).

Figure 4:
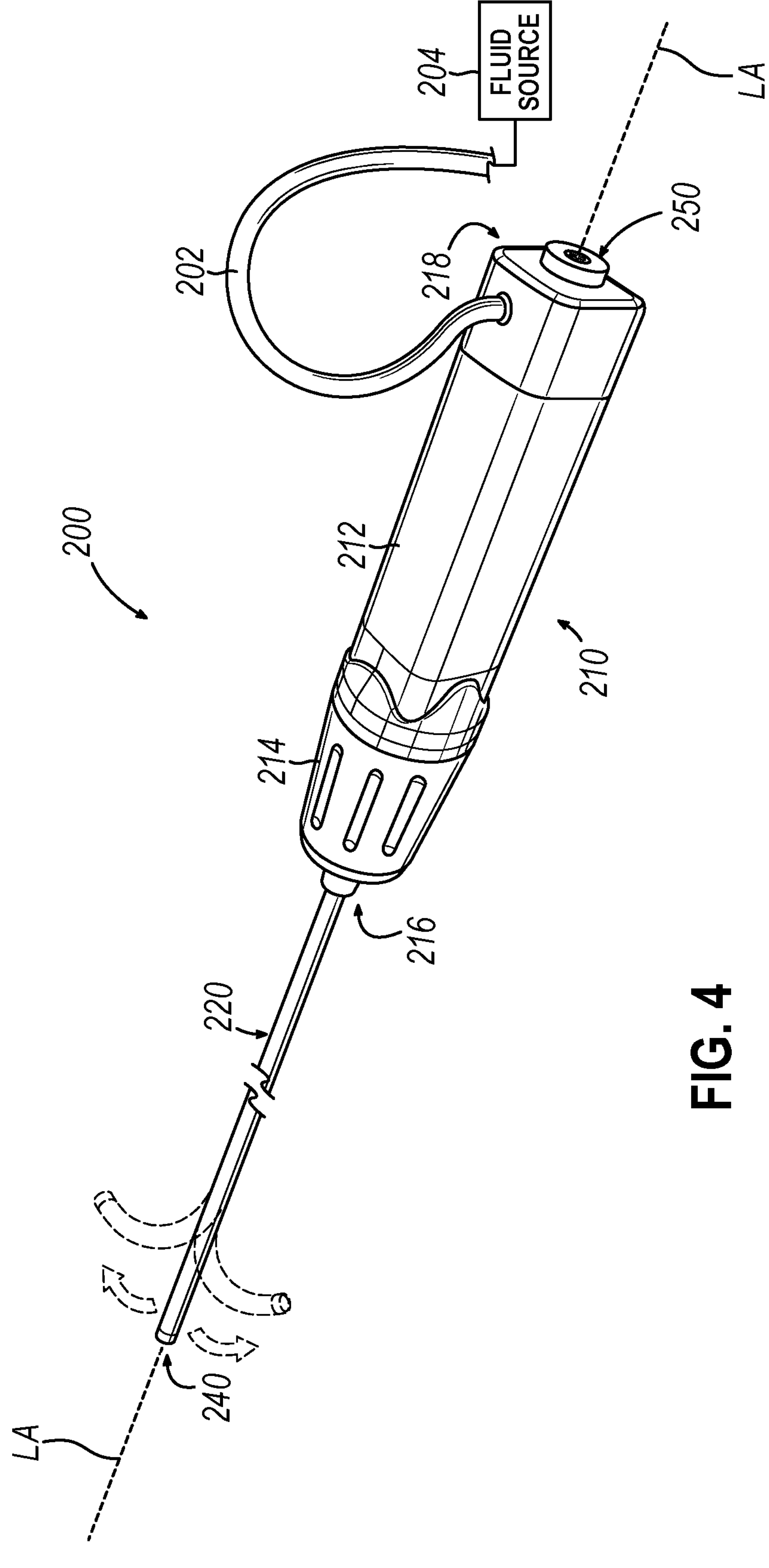
FIG. 4 depicts a perspective view of an example of a guiding sheath that may be used with the catheter assembly of FIG. 1.
Figures 5, 6, 7:
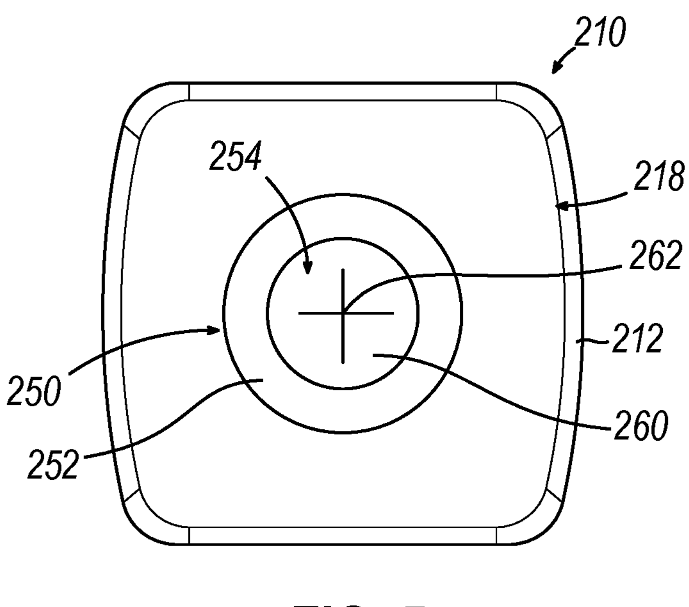
FIG. 5 depicts an end view of the proximal end of the guiding sheath of FIG. 4.
FIG. 6 depicts a perspective view of an example of an insert member that may be used with the catheter assembly of FIG. 1 and the guiding sheath of FIG. 4.
FIG. 7 depicts an end view of the proximal end of the insert member of FIG. 6.

FIGS. 4-5 show an example of a guiding sheath (200) that may be used in such procedures. Guiding sheath (200) of this example includes a handle assembly (210) with a hollow shaft (220) extending distally from a distal end (216) of handle assembly (210). Handle assembly (210) is configured for grasping by a casing (212). The open distal end (240) of the hollow shaft (220) is operable to deflect laterally away from a longitudinal axis (LA) of the shaft. This deflection is controlled by a rotary knob (214) at distal end (216) of handle assembly (210). Rotary knob (214) is rotatable relative to casing (212), about the longitudinal axis (LA), to thereby actuate components that drive lateral deflection of open distal end (240) of hollow shaft (220). By way of example only, such actuation components may include one or more pull wires, bands, or any other suitable structures as will be apparent to those skilled in the art in view of the teachings herein.

As shown in FIG. 4, a tube (202) extends laterally from the proximal end (218) of handle assembly (210). Tube (202) of this example is in fluid communication with a hollow interior (not shown) defined within handle assembly (210), with the hollow interior being in fluid communication with the interior of hollow shaft (220). Tube (202) of the present example is further in fluid communication with a fluid source (204). By way of example only, fluid source (204) may contain saline or any other suitable fluid. In some instances, fluid from fluid source (204) is communicated through tube (202), a hollow interior region defined within handle assembly (210), and the interior of hollow shaft (220), to thereby flush the fluid path defined by tube (202), the hollow interior region defined within handle assembly (210), and the interior of hollow shaft (220).

As shown in FIGS. 4-5, proximal end (218) of handle assembly (210) further includes an insertion port (250). Insertion port (250) is aligned with the longitudinal axis (LA) and provides a port for inserting end effector (140) and catheter (120) into hollow shaft (220) as will be described in greater detail below. Insertion port (250) of this example includes an annular protrusion (252) defining an opening (254). Protrusion (252) protrudes proximally from casing (212) at proximal end (218). In some versions, protrusion (252) is omitted.

A seal (260) is positioned within opening (254). By way of example only, seal (260) may include an elastomeric membrane or other kind of component(s) as will be apparent to those skilled in the art in view of the teachings herein. Seal (260) of the present example further includes a slit arrangement (262) that is configured to facilitate insertion of an instrument (e.g., catheter (120) or an insert member (300) as described below, etc.) through seal (260). In the present example, slit arrangement (262) is in the form of a "+" sign, though any other suitable kind of configuration may be used. When nothing is inserted through seal (260), seal (260) is configured to provide a fluid-tight seal that prevents fluid from escaping the portion of the above-described fluid path defined within handle assembly (210) via insertion port (250); and prevents air from entering the above-described fluid path defined within handle assembly (210) via insertion port (250). When an instrument is inserted through seal (260), seal (260) still substantially maintains a fluid-tight seal of port (250), preventing fluid from escaping the above-described fluid path defined within handle assembly (210) via insertion port (250); and preventing air from entering above-described fluid path defined within handle assembly (210) via insertion port (250), while still allowing the inserted instrument to translate relative to seal (260). Thus, regardless of whether an instrument is disposed in insertion port (250), seal (260) may prevent fluids from leaking out through insertion port (250) and prevent air from being aspirated into the heart (H) of the patient (PA) via insertion port (250).

IV. EXAMPLE OF CYLINDRACEOUS INSERT MEMBER WITH FLARED END

In some procedures, end effector (140) and catheter (120) may be inserted directly into insertion port (250) in order to enter shaft (220) and thereby exit distal end (240) of shaft (220). In some such procedures, a rigid cylindrical insert member is first inserted through seal (260) at slit arrangement (262); and end effector (140) and catheter (120) are then advanced distally through the hollow interior of the cylindrical insert member. The cylindrical insert may assist in providing initial penetration of seal (260) for end effector (140) and catheter (120), which may otherwise be rather difficult for relatively small diameter end effectors (140) and catheters (120). Such a cylindrical insert member may be shaped as a pure cylinder (e.g., a straight tube with a uniform inner and outer diameter along its full length). Catheter assembly (100) may be advanced distally to a point where nozzle member (116) of handle assembly (110) reaches the proximal end of the cylindrical insert member. In such cases, the rigid proximal end of the cylindrical insert member may provide strain on the proximal end of catheter (120), which may be undesirable as the strain may compromise the structural integrity of catheter (120). Similarly, the rigid proximal end of the cylindrical insert member may encourage the formation of kinks at the proximal end of catheter (120). It may therefore be desirable to provide a version of an insert member that eliminates or otherwise reduces the risk of strain or kinking in catheter (120) at the proximal end of the insert member.

In some cases where a cylindrical insert member is used, the operator may inadvertently insert the cylindrical insert member through insertion port (250) too far, to the point where the proximal end of the cylindrical insert member passes fully through seal (260). This may be a particular risk in instances where the physician (PH) uses a catheter (120) and cylindrical insert member with a size (e.g., 8 French) that is smaller than the size of catheter and cylindrical insert member (e.g., 10 French) that guiding sheath (200) was intended to be used with. In some instances where the proximal end of the cylindrical insert member passes distally beyond seal (260), it may be difficult or impossible to remove the cylindrical insert member from handle assembly (210). In addition, or in the alternative, having an insert member jammed in seal (260) may prevent seal (260) from providing a fluid-tight seal at insertion port (250), such that air or other fluids may leak through insertion port (250). In a worst-case scenario, the cylindrical insert member may further pass through shaft (220) of guiding sheath (200) and exit distal end (216), such that the cylindrical insert member is undesirably deposited into the patient (PA). It may therefore be desirable to provide a version of an insert member that eliminates or otherwise reduces the risk of the insert member passing fully through seal (260) or other portions of insertion port (250).

FIGS. 6-7 show an example of an insert member (300) that may be used to assist in inserting end effector (140) and catheter (120) through insertion port (250) of guiding sheath (200). Insert member (300) of this example includes a cylindrical distal portion (302) and a flared proximal portion (304). Distal portion (302) is in the form of a straight cylinder shaft and defines a lumen (320) that proximally terminates at flared proximal portion (304) and distally terminates at distal end (310) of insert member (300). Proximal portion (304) has a frustoconical shape leading into lumen (320) and defines proximal end (312) of insert member (300). Proximal portion (304) thus tapers inwardly toward the central longitudinal axis (LA) of insert member (300) in the proximal-to-distal direction. In the present example, insert member (300) is substantially rigid.

Figure 8:
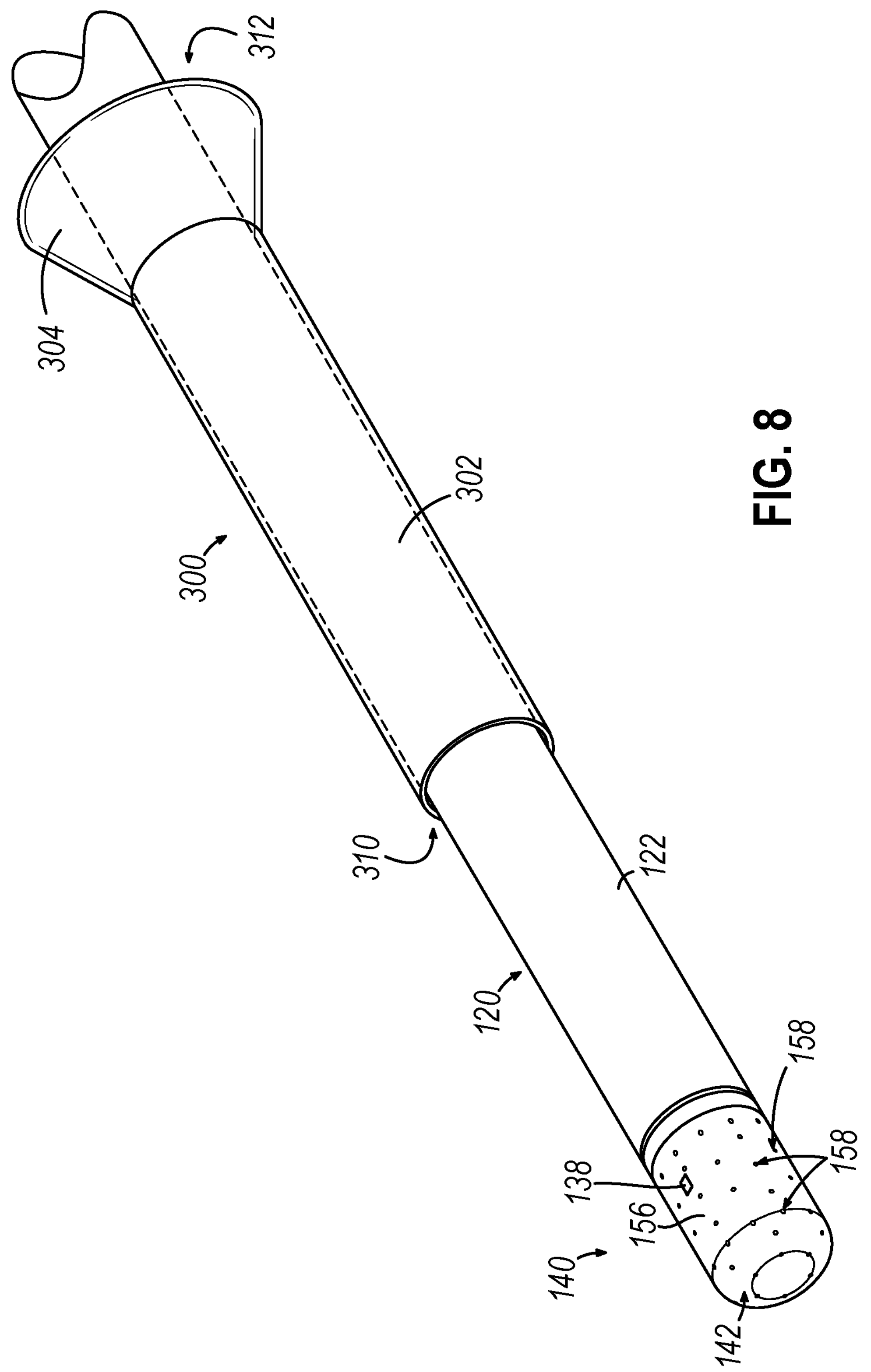
FIG. 8 depicts a perspective view of the insert member of FIG. 6 disposed on a distal portion of a catheter of the catheter assembly of FIG. 1.

Insert member (300) is configured to receive end effector (140) and catheter (120), as shown in FIG. 8. Lumen (320) is sized to closely complement the outer diameter of catheter (120) while permitting catheter (120) to slide freely through insert member (300). The frustoconical shape of proximal portion (304) may provide a lead-in that further assists in insertion of end effector (140) and catheter (120) into proximal end (312) of insert member (300). As also shown in FIG. 8, the length of insert member (300) is substantially less than the length of catheter (120), such that end effector (140) protrudes distally past distal end (310) of insert member (300) while insert member (300) is disposed about catheter (120).

Figure 9A:
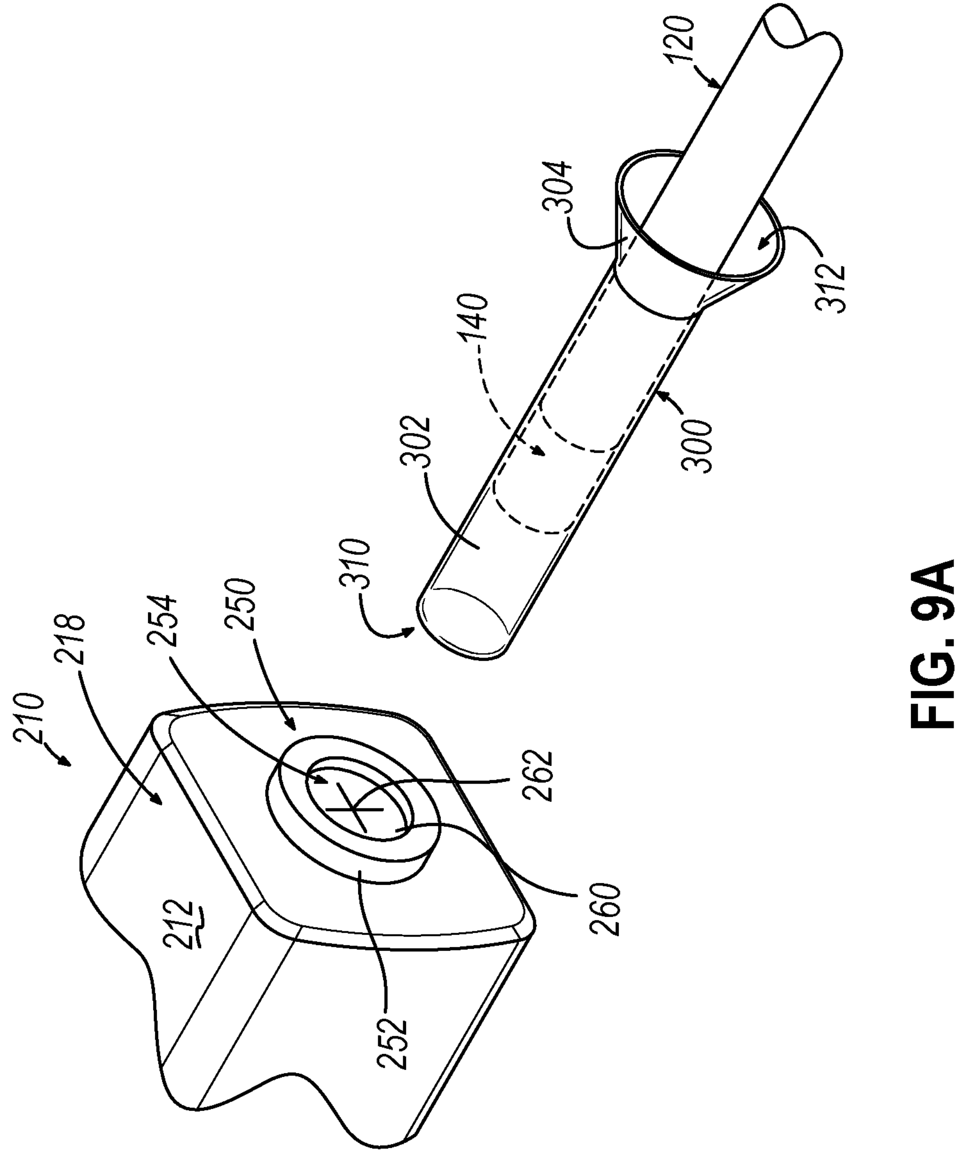
FIG. 9A depicts a perspective view of the insert member of FIG. 6 disposed on a distal portion of a catheter of the catheter assembly of FIG. 1, with the insert member and catheter positioned for insertion in the proximal end of the guiding sheath of FIG. 4.

In an example of use of insert member (300), insert member (300) may first be partially disposed about end effector (140) and the distal end of catheter (120) as shown in FIG. 9A. The combination of insert member (300), end effector (140), and catheter (120) may be positioned for insertion into insertion port (250). Thus, the longitudinal axis (LA) of catheter (120) may be aligned with the longitudinal axis (LA) of guiding sheath (200). At this stage in the present example, end effector (140) is longitudinally disposed between distal end (310) of insert member (300) and proximal end (312) of insert member (300).

Figure 9B:
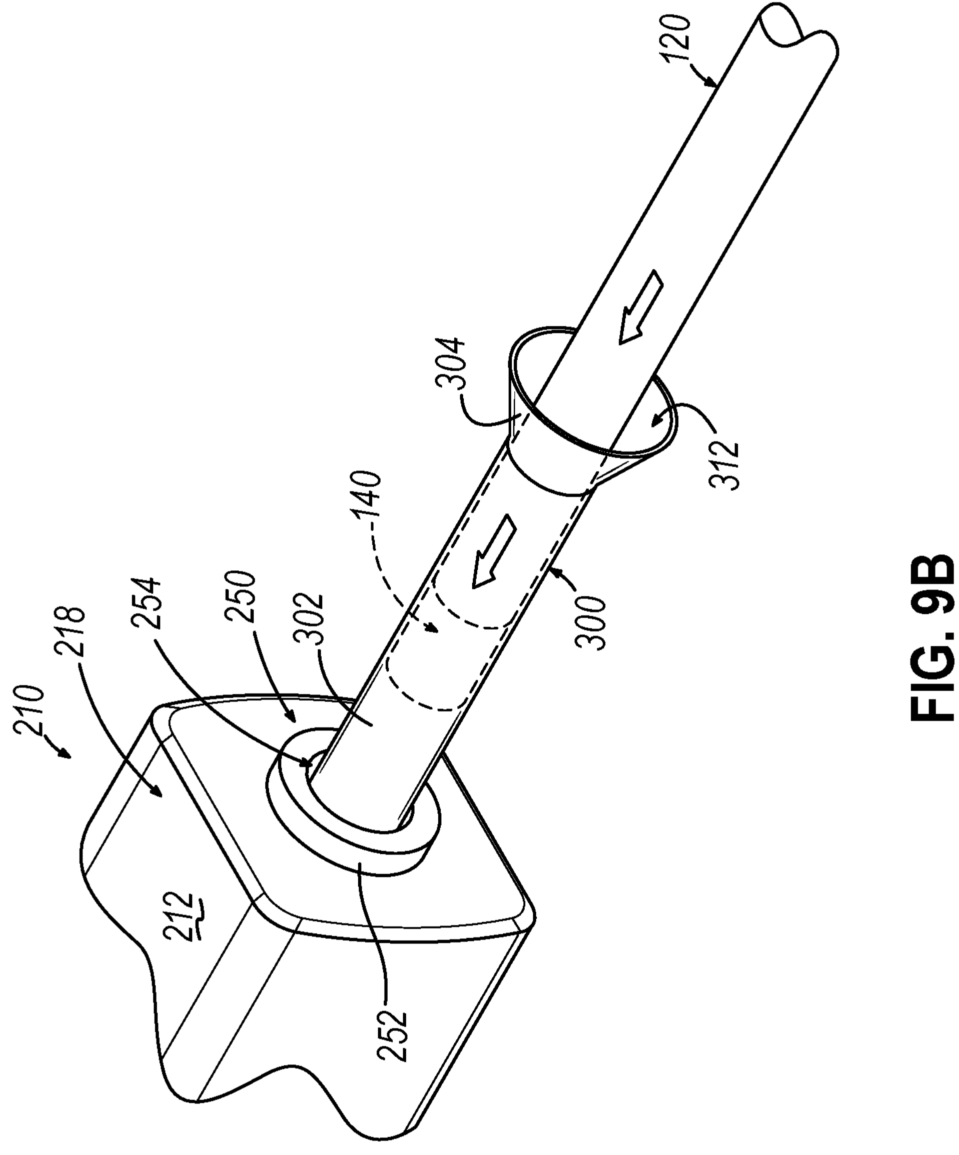
FIG. 9B depicts a perspective view of the insert member of FIG. 6 disposed on a distal portion of a catheter of the catheter assembly of FIG. 1, with the insert member being inserted into the proximal end of the guiding sheath of FIG. 4, and with the catheter not yet inserted into the proximal end of the guiding sheath.
Figure 9C:
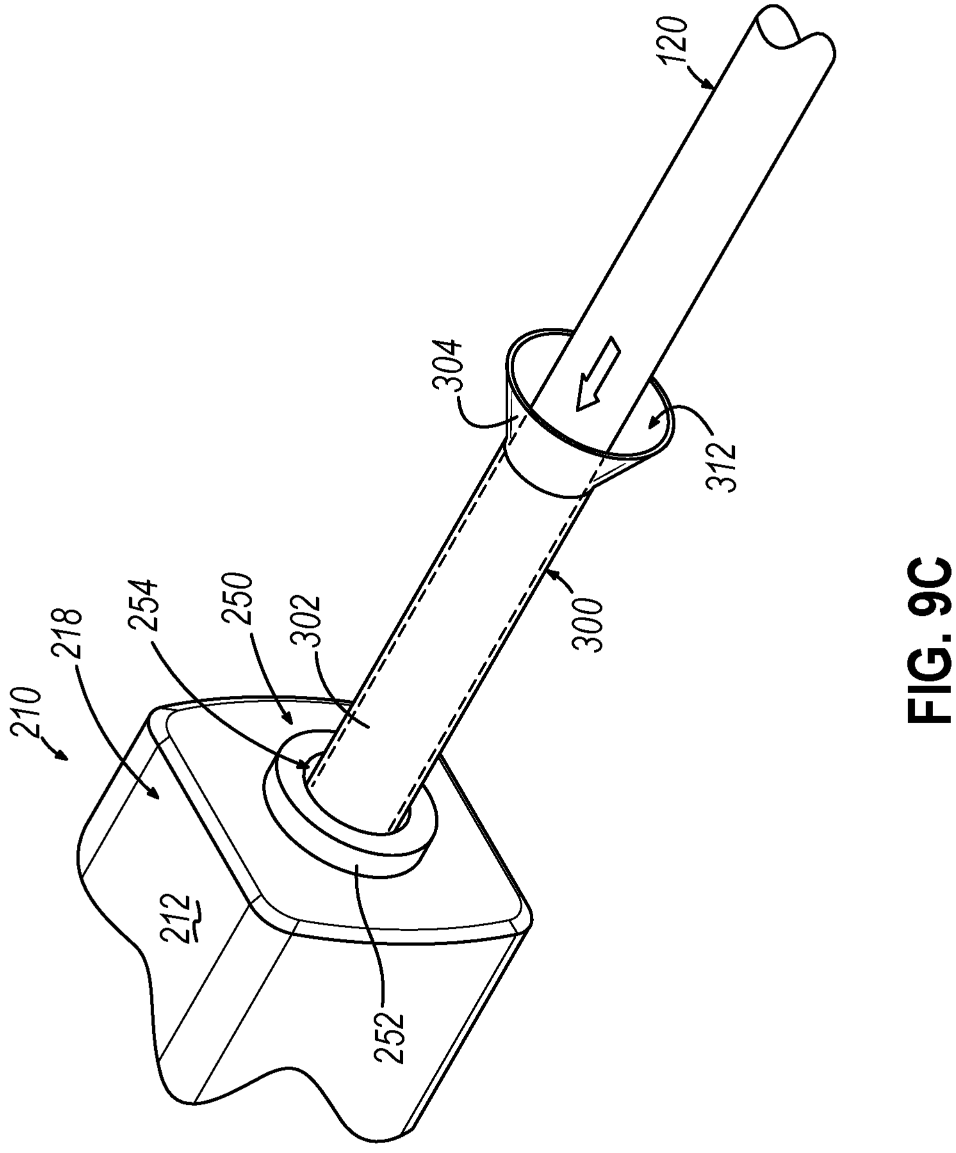
FIG. 9C depicts a perspective view of the insert member of FIG. 6 disposed on a distal portion of a catheter of the catheter assembly of FIG. 1, with the insert member and the catheter both inserted into the proximal end of the guiding sheath of FIG. 4.

Next, the physician may advance the combination of insert member (300), end effector (140), and catheter (120) distally toward insertion port (250), such that distal end (310) of insert member (300) penetrates seal (260) at slit arrangement (262), as shown in FIG. 9B. In this example, distal end (310) of insert member (300) passes through seal (260) before end effector (140) is advanced distally beyond distal end (310) of insert member (300). Once distal end (310) of insert member (300) has passed through seal (260), catheter (120) is advanced such that end effector (140) is advanced distally beyond distal end (310) of insert member (300), as shown in FIG. 9C. As catheter (120) is advanced, end effector (140) and catheter (120) pass distally through the interior of shaft (220). End effector (140) eventually reaches a point where end effector (140) is distal to distal end (240) of shaft (220). In some versions of the procedure, after reaching the state shown in FIG. 9C, insert member (300) is retracted proximally relative to catheter (120) as the physician (PA) continues to advance catheter (120) distally. In other words, distal end (310) of insert member (300) may be proximal to insertion port (250) during at least part of the procedure where catheter (120) is advanced distally into guiding sheath (200).

In some scenarios, during normal operation of catheter assembly (100) and guiding sheath (200), when end effector (140) is positioned distally relative to distal end (240) of shaft (220), nozzle member (116) of handle assembly (110) and insert member (300) are both spaced proximally away from insertion port (250). Thus, some versions of catheter assembly (100), guiding sheath (200), and insert member (300) may be configured to allow end effector (140) to be distally exposed from shaft (220) and thus operated within the heart (H) of the patient (PA), without insert member (300) needing to contact insertion port (250); and without nozzle member (116) needing to contact insert member (300). In such scenarios, insert member (300) may simply be positioned about a region of catheter (120) that is longitudinally interposed between insertion port (250) and nozzle member (116) of handle assembly (110).

Figure 9D:
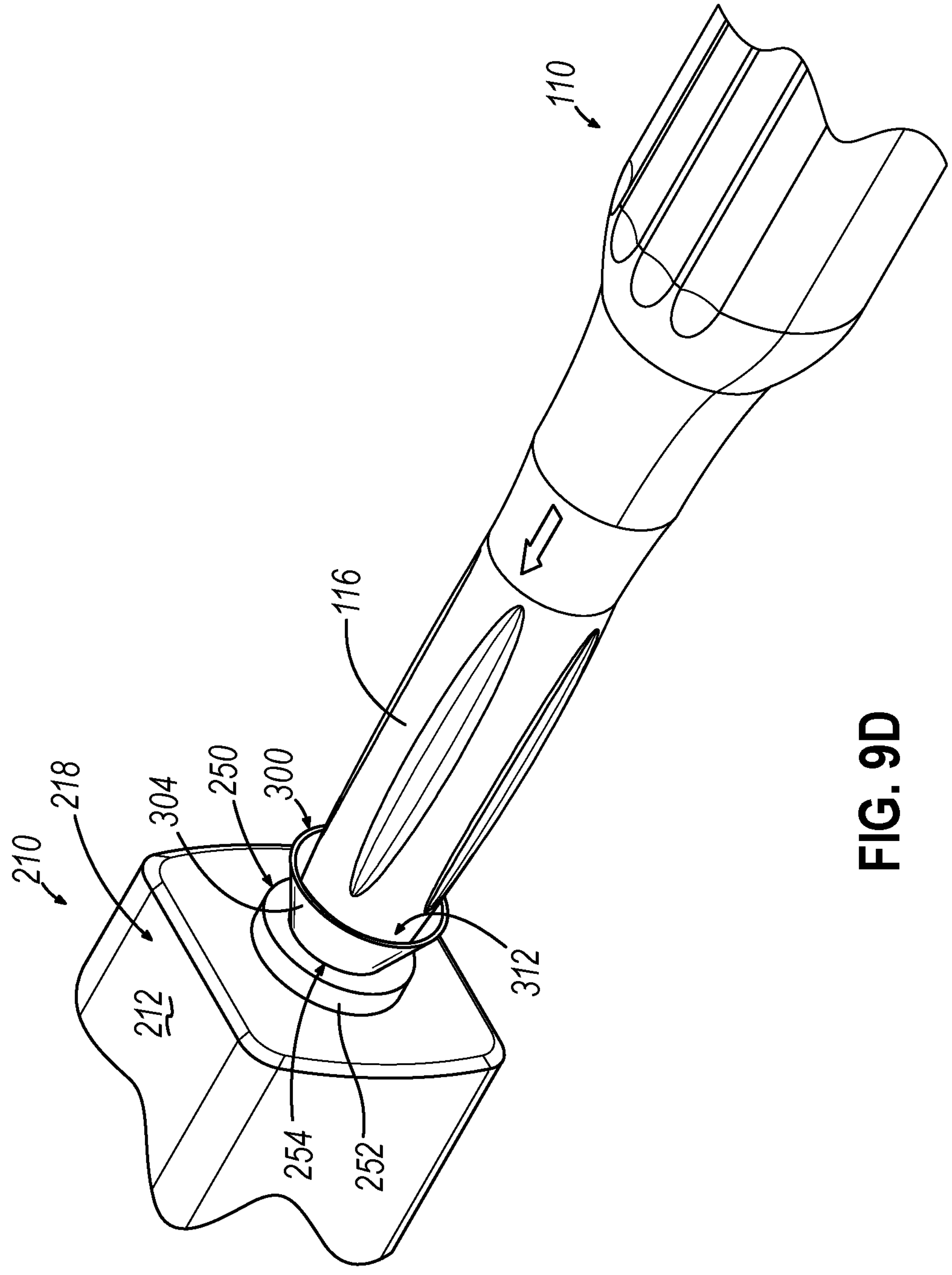
FIG. 9D depicts a perspective view of the insert member of FIG. 6 fully inserted into the guiding sheath of FIG. 4, and with the insert member arresting insertion of the catheter assembly of FIG. 1 into the guiding sheath.

In the event that the physician (PA) continues to advance catheter assembly (100) distally to the point where nozzle member (116) of handle assembly (110) engages insert member (300), flared proximal portion (304) of insert member (300) may eventually engage annular protrusion (252) of insertion port (250) as shown in FIG. 9D. While cylindrical distal portion (302) of insert member (300) has an outer diameter that is smaller than the diameter of opening (254), flared proximal portion (304) of insert member (300) has an outer diameter that is larger than the diameter of opening (254). Thus, flared proximal portion (304) of insert member (300) will engage annular protrusion (252) of insertion port (250), and this interaction between flared proximal portion (304) of insert member (300) and annular protrusion (252) of insertion port (250) will arrest insert member (300) and thereby prevent insert member (300) from advancing further distally into insertion port (250).

While flared proximal portion (304) of insert member (300) engages annular protrusion (252) of insertion port (250) in the foregoing example, other configurations may provide engagement between flared proximal portion (304) and seal (260). In such scenarios, annular protrusion (252) may simply be absent. Alternatively, flared proximal portion (304) may have an outer diameter that is sized to pass through the opening defined by annular protrusion (252) but not through seal (260). In either case, slit arrangement (262) may be configured to permit cylindrical distal portion (302) of insert member (300) through seal (260) but prevent flared proximal portion (304) of insert member (300) from passing through seal (260). As another merely illustrative alternative, insertion port (250) may include some other structure that engages annular protrusion (252) and thereby arrests insertion of insert member (300) through insertion port (250).

In addition to arresting distal insertion of insert member (300) into insertion port (250), flared proximal portion (304) of insert member (300) may further eliminate or otherwise reduce strain that might otherwise occur at the junction of the proximal end (312) of insert member (300) and catheter (120) by providing greater freedom of catheter (120) to deflect laterally relative to proximal end (312) of insert member (300).

In some variations of the procedure described above, insert member (300) is inserted into insertion port (250) before end effector (140) and catheter (120) are inserted into insert member (300). In other words, end effector (140) and catheter (120) may be fully decoupled from insert member (300) when insert member (300) is initially inserted into insertion port (250). In some such variations of the procedure, insert member (300) is first fully inserted into insertion port (250), to the point where flared proximal portion (304) of insert member (300) engages annular protrusion (252) of insertion port (250), before end effector (140) and catheter (120) are inserted into insert member (300).

V. EXAMPLE OF CYLINDRACEOUS INSERT MEMBER WITH SEALING MEMBER

As noted above, it may be desirable to prevent air from entering the heart (H) of the patient (PA) via insertion port (250). To the extent that seal (260) substantially prevents air from entering the heart (H) of the patient (PA) via insertion port (250), there may be some instances where an insert member (300) is disposed in insertion port (250), and a catheter (120) is disposed in lumen (320) of insert member (300), and air is able to pass through a gap defined between the inner diameter of insert member (300) and the outer diameter of catheter (120). It may therefore be desirable to provide a modified form of insert member (300) that includes a feature to effectively close such a gap. An example of a modified form of insert member (300) is shown in FIGS. 10-12B.

FIGS. 10-12B show an insert member (400) that may be used in a manner similar to that described above for insert member (300). Insert member (400) of this example includes a cylindrical distal portion (402) and a flared proximal portion (404). Distal portion (402) is in the form of a straight cylinder defining a lumen (420) that proximally terminates at flared proximal portion (404) and distally terminates at distal end (410) of insert member (400). Proximal portion (404) has a frustoconical shape leading into lumen (420) and defines proximal end (412) of insert member (400). In the present example, insert member (400) is substantially rigid.

Unlike insert member (300), insert member (400) of the present example further includes a seal member (450) that is positioned in lumen (420). Seal member (450) is formed of a biocompatible elastomeric material (e.g., rubber, silicone, etc.). In some other versions, seal member (450) is not necessarily elastomeric, but may have a durometer that is lower than the durometer of cylindrical portion (402). Seal member (450) includes a cylindraceous body (452) with a plurality of integral tabs (454) extending radially outwardly from body (452). Tabs (454) are disposed in lateral openings (406) that are formed through cylindrical distal portion (402) of insert member (400). Tabs (454) thus secure the position of seal member (450) within cylindrical distal portion (402). Alternatively, any other suitable structures or techniques may be used to secure the position of seal member (450) within cylindrical distal portion (402).

Seal member (450) further includes a pair of ramped internal surfaces (456) that converge at a ridge (458) at the longitudinal center of seal member (450). Ridge (458) defines an inner diameter that is less than the outer diameter of catheter (120). Thus, when catheter (120) is inserted through insert member (400) as shown in FIG. 12B, seal member (450) deforms against the outer diameter of catheter (120). Seal member (450) thus forms a fluid tight seal between the inner diameter of cylindrical distal portion (402) and the outer diameter of catheter (120). This seal prevents air from passing between inner diameter of cylindrical distal portion (402) and the outer diameter of catheter (120) to reach the heart (H) of the patient (PA). While seal member (450) forms a fluid tight seal against catheter (120), seal member (450) may nevertheless permit catheter (120) to translate through insert member (400). Insert member (400) may thus be used just like insert member (300) as described above in the context of FIGS. 9A-9D.

While seal member (450) is shown as being positioned near the longitudinal center of insert member (400) in the present example, seal member (450) may instead be positioned at any other suitable location along the length of insert member (400). For instance, seal member (450) may instead be positioned near distal end (410). Alternatively, seal member (450) may be positioned closer to the transition from cylindrical distal portion (402) to flared proximal portion (404).

Figure 13:
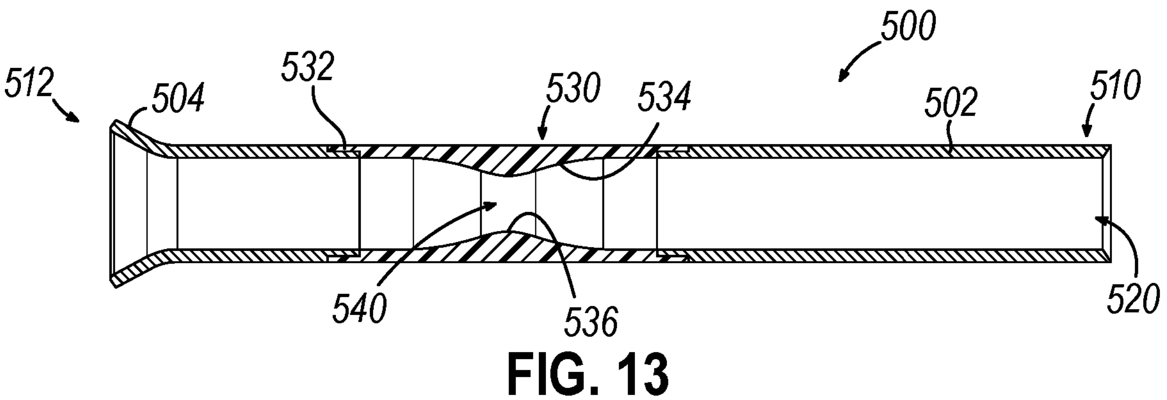
FIG. 13 depicts a cross-sectional side view of another example of an insert member that may be used with the catheter assembly of FIG. 1 and the guiding sheath of FIG. 4.

FIG. 13 shows another example of an insert member (500) that may be used in a manner similar to that described above for insert member (300). Insert member (500) of this example includes a cylindrical distal portion (502) and a flared proximal portion (504). Distal portion (502) is in the form of a straight cylinder defining a lumen (520) that proximally terminates at flared proximal portion (504) and distally terminates at distal end (510) of insert member (500). Proximal portion (504) has a frustoconical shape leading into lumen (520) and defines proximal end (512) of insert member (500). In the present example, insert member (500) is substantially rigid.

Like insert member (400), insert member (500) of the present example includes a seal member (530) that is positioned in lumen (520). Seal member (530) is formed of a biocompatible elastomeric material (e.g., rubber, silicone, etc.). In some other versions, seal member (530) is not necessarily elastomeric, but may have a durometer that is lower than the durometer of cylindrical portion (502). Seal member (530) includes a cylindraceous body (532) that is fixedly secured relative to cylindrical distal portion (502). By way of example only, cylindraceous body (532) may be secured to cylindrical distal portion (502) via structures similar to tabs (454) and openings (406) as described above, via an overmolding process, via an adhesive, or in any other suitable fashion as will be apparent to those skilled in the art in view of the teachings herein.

Seal member (530) further includes a curved internal surface (534) that defines a contoured ridge (536) at the longitudinal center of seal member (530). Ridge (536) defines an opening (540) having a diameter that is less than the outer diameter of catheter (120). Thus, when catheter (120) is inserted through inner lumen (520) of insert member (530), seal member (530) deforms against the outer diameter of catheter (120). Seal member (530) thus forms a fluid tight seal between the inner diameter of cylindrical distal portion (502) and the outer diameter of catheter (120). This seal prevents air from passing between inner diameter of cylindrical distal portion (502) and the outer diameter of catheter (120) to reach the heart (H) of the patient (PA). While seal member (530) forms a fluid tight seal against catheter (120), seal member (530) may nevertheless permit catheter (120) to translate through insert member (500). Insert member (500) may thus be used just like insert member (300) as described above in the context of FIGS. 9A-9D.

Figure 14:
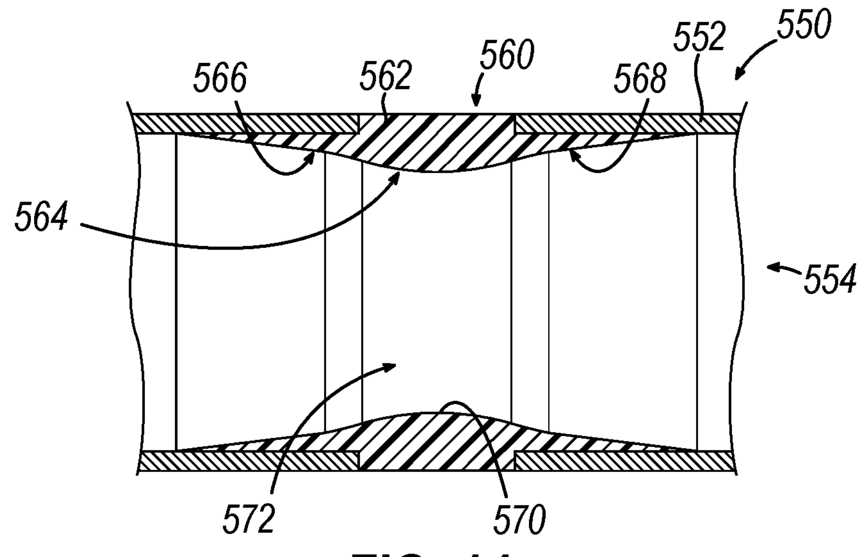
FIG. 14 depicts a cross-sectional side view of an intermediate portion of another example of an insert member that may be used with the catheter assembly of FIG. 1 and the guiding sheath of FIG. 4.

In the example shown in FIG. 13, curved internal surface (534) has the form of a three-dimensional, annular bell curve, with ridge (536) being formed by the peak of the bell curve. This bell curve defined by curved internal surface (534) is symmetric about a transverse plane that bisects seal member (530) at ridge (536). In some other versions, the curve is not symmetric. FIG. 14 shows an example of such a version. FIG. 14 shows an intermediate region of an insert member (550) that includes a seal member (560) disposed in a cylindrical portion (552). While not shown, seal member (560) may also include a flared portion like flared portions (404, 504) described above. Insert member (550) may be configured and operable just like insert member (500), except for the differences described below.

Seal member (560) of insert member (550) is similar to seal member (530) of insert member (500) in that seal member (560) is formed of a biocompatible elastomeric material (e.g., rubber, silicone, etc.); and that seal member (560) includes a cylindraceous body (562) that is fixedly secured relative to cylindrical portion (552). Seal member (560) of insert member (550) is also similar to seal member (530) of insert member (500) in that seal member (560) includes a curved internal surface (564) that defines a contoured ridge (570). Ridge (570) defines an opening (572) having a diameter that is less than the outer diameter of catheter (120), such that seal member (560) may form a fluid-tight seal against the outer diameter of a catheter (120) that is inserted through lumen (554) of insert member (550). Unlike curved internal surface (534) of seal member (530), curved internal surface (564) of seal member (560) is not symmetric about a transverse plane that bisects seal member (560) at ridge (570). Instead, curved internal surface (564) includes a relatively shallow (i.e., larger radius of concave curvature) curved proximal region (566) leading to ridge (570); with a relatively steeper (i.e., smaller radius of concave curvature) curved distal region (568) distal to ridge (570). Moreover, the longitudinal length of proximal region (566) of distal region (568) is longer. This configuration of seal member (560) may provide a smoother insertion path for catheter (120) through opening (572) of seal member (560).

Figure 15:
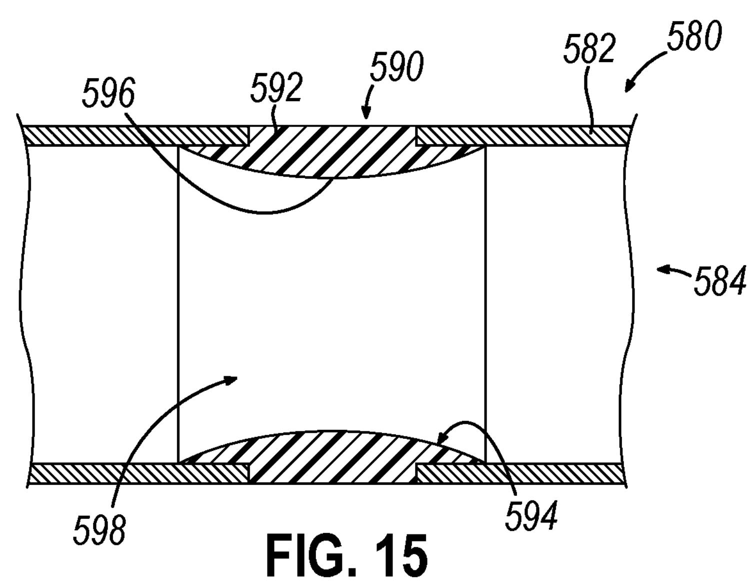
FIG. 15 depicts a cross-sectional side view of an intermediate portion of another example of an insert member that may be used with the catheter assembly of FIG. 1 and the guiding sheath of FIG. 4.

FIG. 15 shows another variation of an insert member (580) that is similar to insert members (400, 500, 550) described above. Insert member (580) of this example includes a seal member (590) disposed in a cylindrical portion (582). While not shown, seal member (580) may also include a flared portion like flared portions (404, 504) described above. Insert member (590) may be configured and operable just like insert member (500), except for the differences described below.

Seal member (590) of insert member (580) is similar to seal member (530) of insert member (500) in that seal member (590) is formed of a biocompatible elastomeric material (e.g., rubber, silicone, etc.); and that seal member (590) includes a cylindraceous body (592) that is fixedly secured relative to cylindrical portion (582). Seal member (590) of insert member (580) is also similar to seal member (530) of insert member (500) in that seal member (590) includes a curved internal surface (594) that defines a contoured ridge (596). Ridge (596) defines an opening (598) having a diameter that is less than the outer diameter of catheter (120), such that seal member (590) may form a fluid-tight seal against the outer diameter of a catheter (120) that is inserted through lumen (584) of insert member (580). Unlike curved internal surface (534) of seal member (530), curved internal surface (564) of seal member (560) is not shaped like a bell curve. Instead, curved internal surface (564) is arcuate, defined by a single, constant radius of curvature. Internal surface (564) thus lacks a concave aspect and is only convex. Seal member (590) may thus provide a sealing interface against the outer diameter of a catheter (120) that is similar to a sealing interface that would be provided by an o-ring or other toroidal shaped sealing member. Seal member (590) may nevertheless function substantially similar to seal members (406, 530, 560) described above. In the present example, the curve defined by curved internal surface (564) is symmetric about a transverse plane that bisects seal member (530) at ridge (536). In some other versions, the curve is not symmetric.

Figure 16:
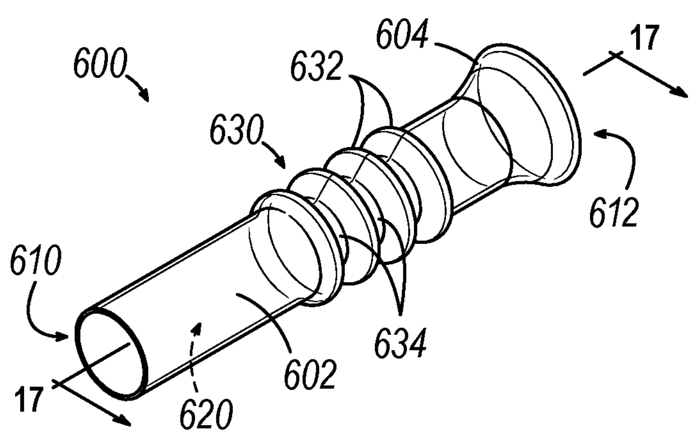
FIG. 16 depicts a perspective view of another example of an insert member that may be used with the catheter assembly of FIG. 1 and the guiding sheath of FIG. 4.
Figure 17A:
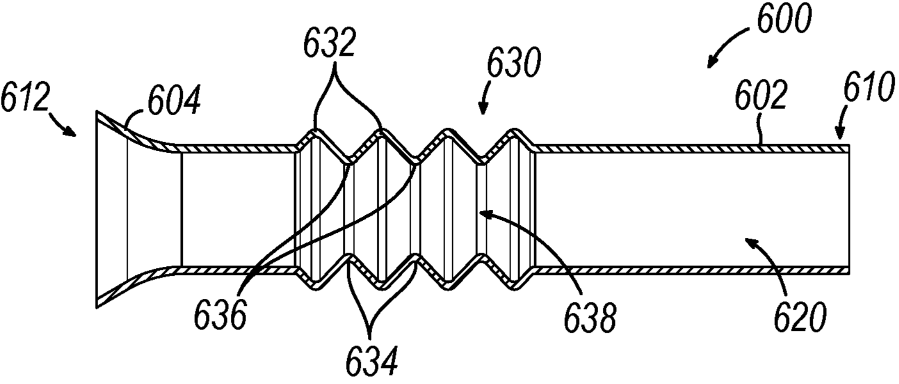
FIG. 17A depicts a cross-sectional view of the insert member of FIG. 16, taken along line 17-17 of FIG. 16.
Figure 17B:
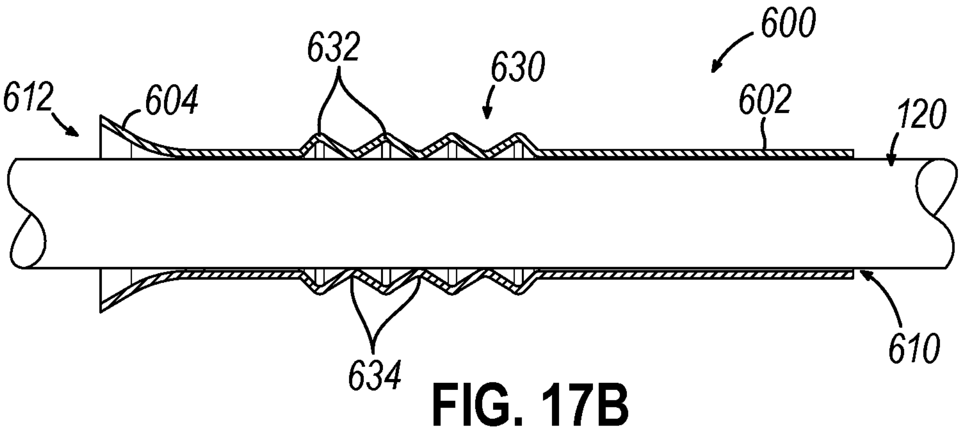
FIG. 17B depicts a cross-sectional view of the insert member of FIG. 16, taken along line 17-17 of FIG. 16, with the catheter of the catheter assembly of FIG. 1 disposed in the insert member.

FIGS. 16-17B show yet another example of an insert member (600) having a seal member (630) in an intermediate region of the length of insert member (600). Insert member (600) of this example includes a cylindrical distal portion (602) and a flared proximal portion (604). Distal portion (602) is in the form of a straight cylinder defining a lumen (620) that proximally terminates at flared proximal portion (604) and distally terminates at distal end (610) of insert member (600). Proximal portion (604) has a frusto-conical shape leading into lumen (620) and defines proximal end (612) of insert member (600). In the present example, insert member (600) is substantially rigid.

Seal member (630) of this example has an accordion-shaped or corrugated profile defined by longitudinally spaced series of annular peaks (632) and adjacent valleys (634). Within lumen (620), valleys (634) form a plurality of internal ridges (636) that together define a passageway (638) having a diameter that is less than the outer diameter of catheter (120). As shown in FIG. 17B, when a catheter (120) is inserted through lumen (620), the outer diameter of catheter (120) bears against ridges (636). Seal member (630) has sufficient flexibility to deform and thereby accommodate insertion of catheter (120) through passageway (638), though seal member (630) also has sufficient resilience to bear against catheter (120) when catheter (120) id disposed in passageway (638). Seal member (630) thus forms a fluid tight seal against catheter (120).

In some versions, seal member (630) is formed of the same material forming the rest of insert member (600), but with reduced wall thickness to accommodate deformation imposed by catheter (120) as described above. In some other versions, seal member (630) is formed of an elastomeric material that is secured to the rest of insert member (600) in any other suitable fashion. Instead of being formed of an elastomeric material, seal member (630) may be formed of the same material forming the rest of insert member (600), but with an elastomeric coating at the interior of seal member (630). In some such versions, the elastomeric coating may deform in response to insertion of catheter (120) through passageway (638), without peaks (632) or valleys (634) necessarily deforming as well. In still other versions, seal member (630) is not necessarily elastomeric, but may have a durometer that is lower than the durometer of cylindrical portion (602). Seal member (630) and cylindrical portion (602) may be formed simultaneously from different materials via a coextrusion or using any other suitable process. Other suitable ways in which seal member (630) may be formed and configured will be apparent to those skilled in the art in view of the teachings herein.

In addition to, or in lieu of, using the various kinds of sealing structures described above, a seal member may instead include any other suitable kind of structure to seal against the outer surface of catheter (120). Such alternative structures may include (but are not limited to) annular wipers, membranes with one or more slits formed there-through, or any other suitable structures as will be apparent to those skilled in the art in view of the teachings herein.

VI. EXAMPLE OF CYLINDRACEOUS INSERT MEMBER WITH ENHANCED STRUCTURAL SUPPORT

In some scenarios, an insert member like insert member (300, 400, 500, 550, 580, 600) may tend to deform (e.g., dent, warp, etc.) in response to transverse loads being applied to insert member (300, 400, 500, 550, 580, 600) during use. Such transverse loads may be applied via catheter (120), via annular protrusion (252) of insertion port (250), or via some other structure. Such deformation may include lateral bending of insert member (300, 400, 500, 550, 580, 600), away from a longitudinal axis of insert member (300, 400, 500, 550, 580, 600). In addition, or in the alternative, such deformation may include radially inward bending of insert member (300, 400, 500, 550, 580, 600), toward a longitudinal axis of insert member (300, 400, 500, 550, 580, 600). In either case, the deformation of insert member (300, 400, 500, 550, 580, 600) may cause insert member (300, 400, 500, 550, 580, 600) to bind against a catheter (120) that is disposed in a longitudinal axis of insert member (300, 400, 500, 550, 580, 600). In addition, or in the alternative, deformation of insert member (300, 400, 500, 550, 580, 600) may otherwise prevent translation of catheter (120) through insert member (300, 400, 500, 550, 580, 600); or otherwise make translation of catheter (120) through insert member (300, 400, 500, 550, 580, 600) more difficult. In view of the foregoing, it may be desirable to add enhanced structural features to an insert member (300, 400, 500, 550, 580, 600) to prevent inadvertent deformation of insert member (300, 400, 500, 550, 580, 600) during use.

Figure 18:
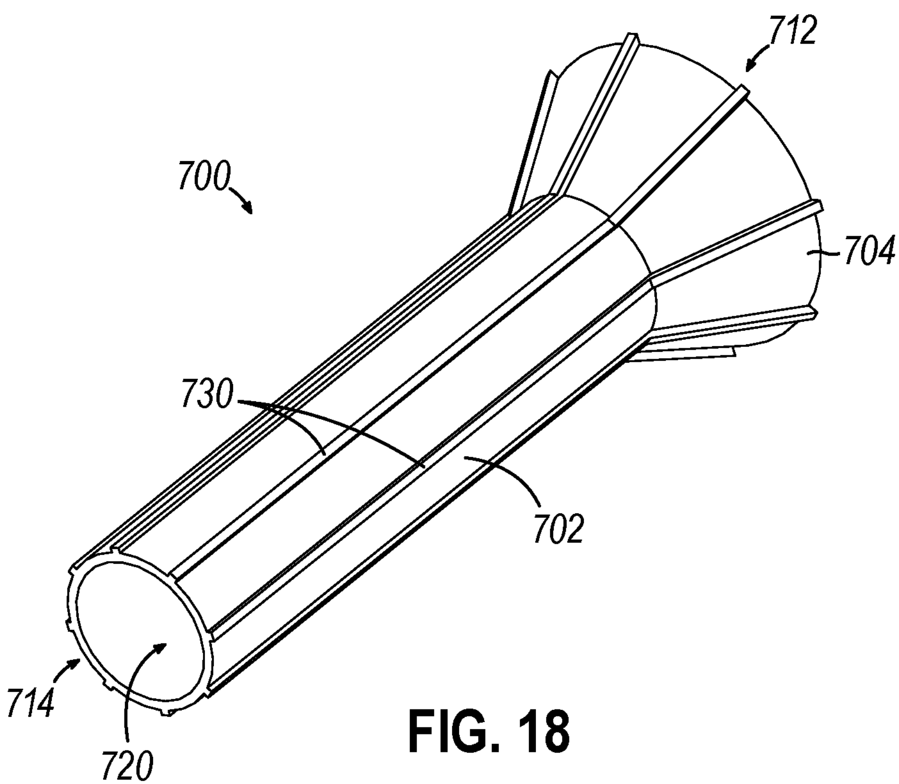
FIG. 18 depicts a perspective view of another example of an insert member that may be used with the catheter assembly of FIG. 1 and the guiding sheath of FIG. 4.
Figure 19:
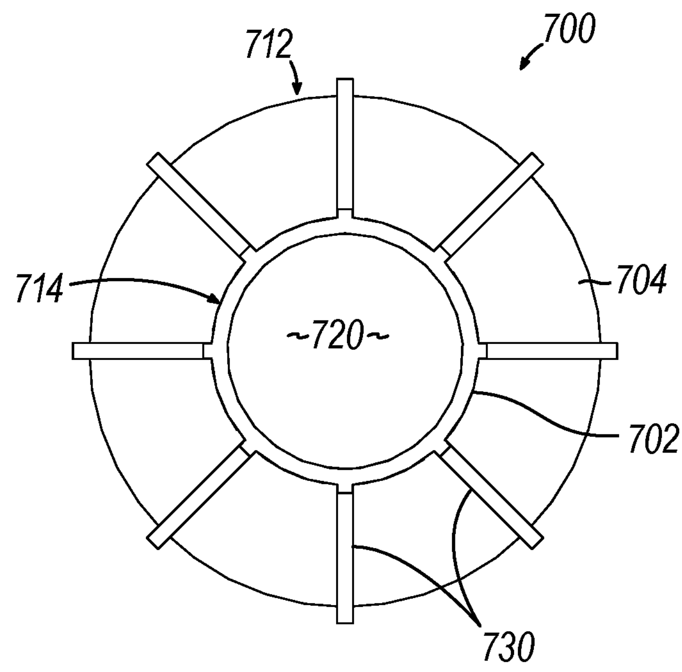
FIG. 19 depicts an end view of the insert member of FIG. 18.

FIGS. 18-19 show an example of an insert member (700) that may be used in a manner similar to that described above for insert member (300). Insert member (700) of this example includes a cylindrical distal portion (702) and a flared proximal portion (704). Distal portion (702) is in the form of a straight cylinder defining a lumen (720) that proximally terminates at flared proximal portion (704) and distally terminates at distal end (714) of insert member (700). Proximal portion (704) has a frustoconical shape leading into lumen (720) and defines proximal end (712) of insert member (700).

In the present example, insert member (700) is substantially rigid. This rigidity is further enhanced by a plurality of longitudinally extending ribs (730). Ribs (730) protrude radially outwardly from the exterior of cylindrical distal portion (702) and flared proximal portion (704). Ribs (730) are angularly spaced equidistantly from each other about the central longitudinal axis of insert member (700). While eight ribs (730) are shown, insert member (700) may instead have more or fewer than eight ribs (730). Insert member (700) may also include any of the various other features described herein, including but not limited to the various seal members (406, 530, 560, 590, 630) described herein. Ribs (730) of the present example are configured to structurally enhance the rigidity of insert member (700), thereby reducing the risk of insert member (700) deforming away from, toward, or about the central longitudinal axis of insert member (700) during use of insert member (700), particularly as insert member (700) is inserted into and retracted from insertion port (250) of guiding sheath (200).

Figure 20:
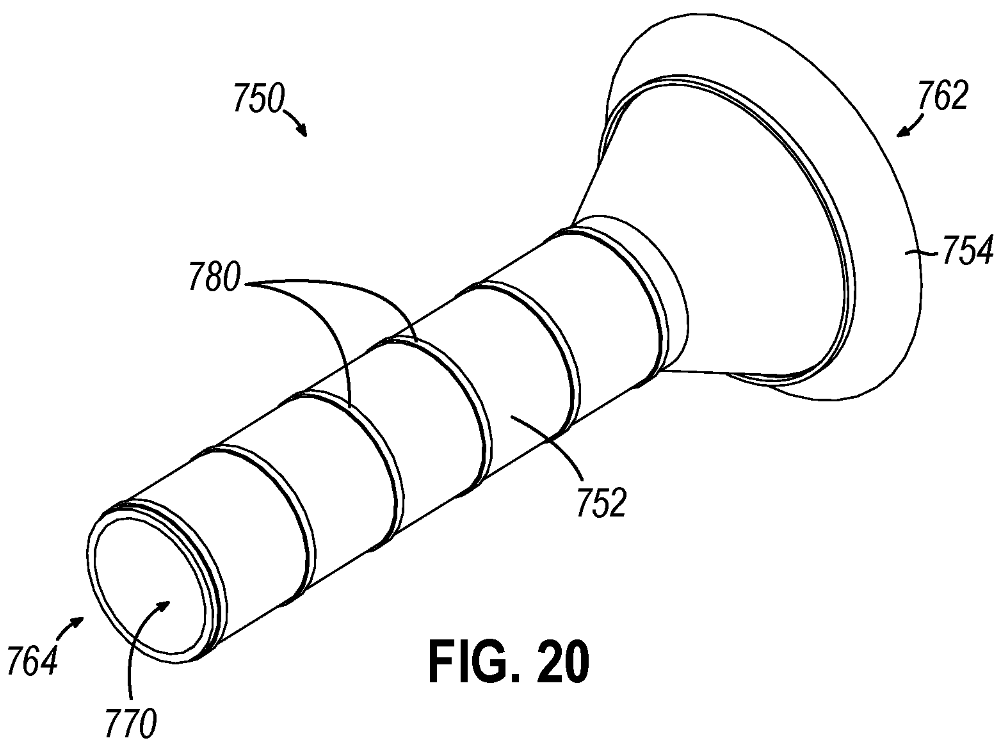
FIG. 20 depicts a perspective view of another example of an insert member that may be used with the catheter assembly of FIG. 1 and the guiding sheath of FIG. 4.
Figure 21:
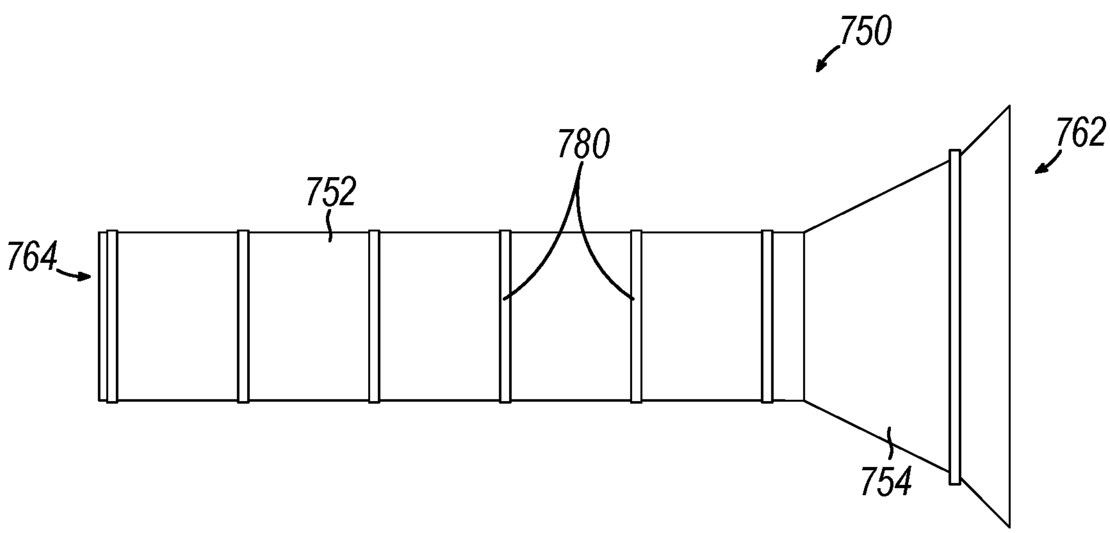
FIG. 21 depicts a side elevation view of the insert member of FIG. 20.

FIGS. 20-21 show another example of an insert member (750) that may be used in a manner similar to that described above for insert member (300). Insert member (750) of this example includes a cylindrical distal portion (752) and a flared proximal portion (754). Distal portion (752) is in the form of a straight cylinder defining a lumen (770) that proximally terminates at flared proximal portion (754) and distally terminates at distal end (764) of insert member (750). Proximal portion (754) has a frustoconical shape leading into lumen (770) and defines proximal end (762) of insert member (750).

In the present example, insert member (750) is substantially rigid. This rigidity is further enhanced by a plurality of angularly extending annular ribs (780). Ribs (780) protrude radially outwardly from the exterior of cylindrical distal portion (752) and flared proximal portion (754). Ribs (780) are longitudinally spaced equidistantly from each other along the central longitudinal axis of insert member (750). While seven ribs (780) are shown, insert member (750) may instead have more or fewer than seven ribs (780). Insert member (750) may also include any of the various other features described herein, including but not limited to the various seal members (406, 530, 560, 590, 630) described herein. In some versions, insert member (750) includes a combination of the longitudinally extending ribs (730) of insert member (700) and annular ribs (780) of insert member (750). Ribs (780) of the present example are configured to structurally enhance the rigidity of insert member (750), thereby reducing the risk of insert member (750) deforming away from or toward the central longitudinal axis of insert member (750) during use of insert member (750), particularly as insert member (750) is inserted into and retracted from insertion port (250) of guiding sheath (200).

While longitudinally extending ribs (730) and annular ribs (780) have been described above as examples of structural enhancement features, an insert member may have structural enhancement features taking any other suitable form. By way of example only, some other structural enhancement features may have a grid configuration, a helical configuration, or any other suitable configuration.

VII. EXAMPLE OF CYLINDRACEOUS INSERT MEMBER WITH TORQUE DRIVING FEATURES

Figure 22:
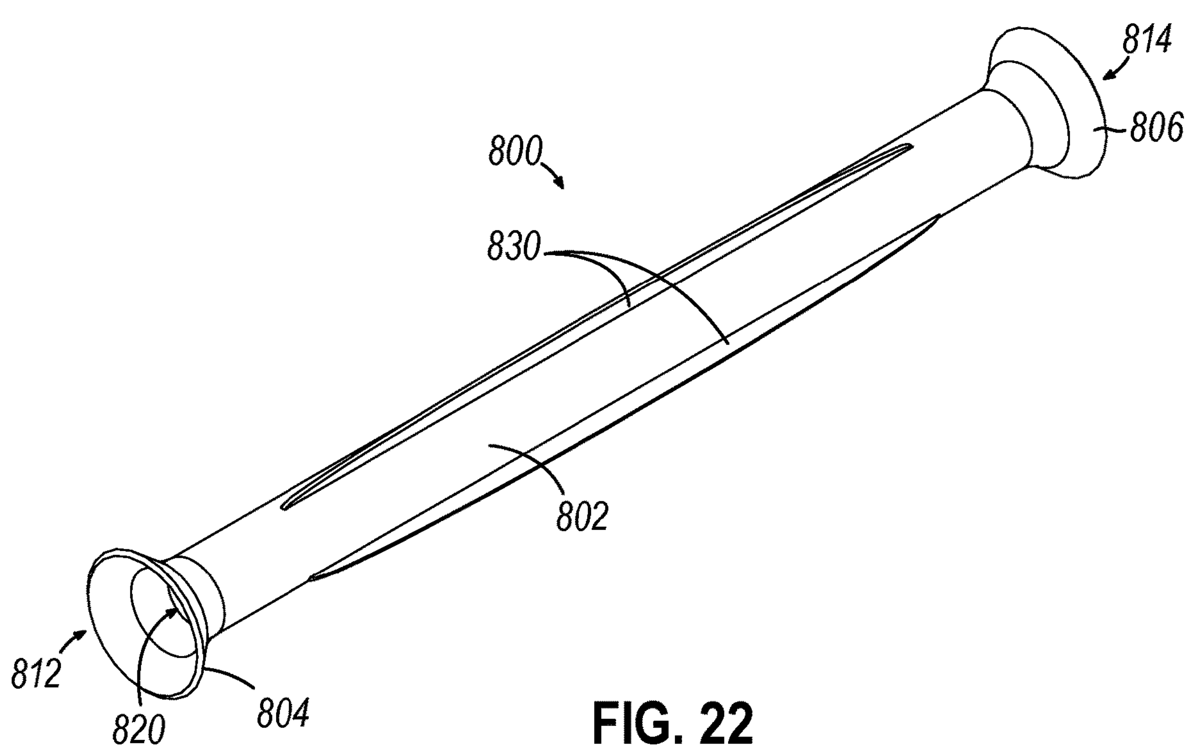
FIG. 22 depicts a perspective view of another example of an insert member that may be used with the catheter assembly of FIG. 1 and the guiding sheath of FIG. 4.
Figure 23:
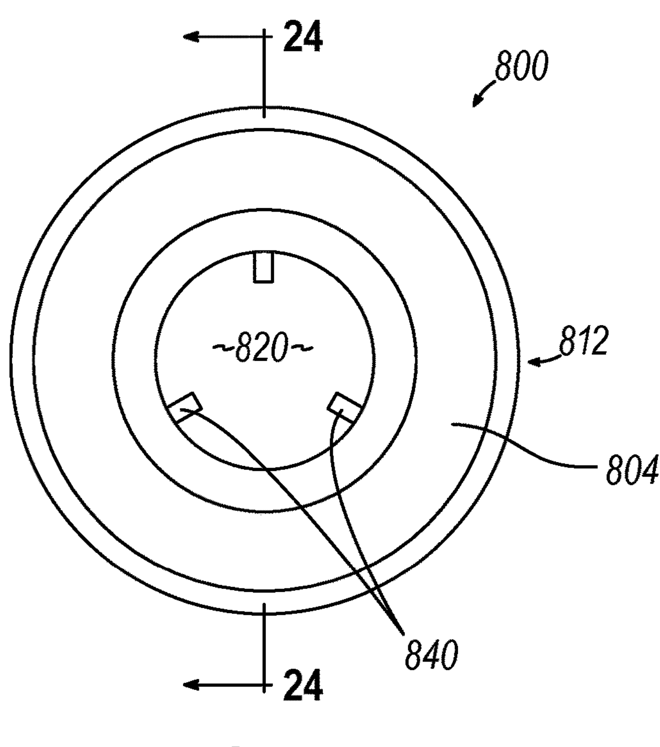
FIG. 23 depicts an end view of the insert member of FIG. 22.
Figure 24:
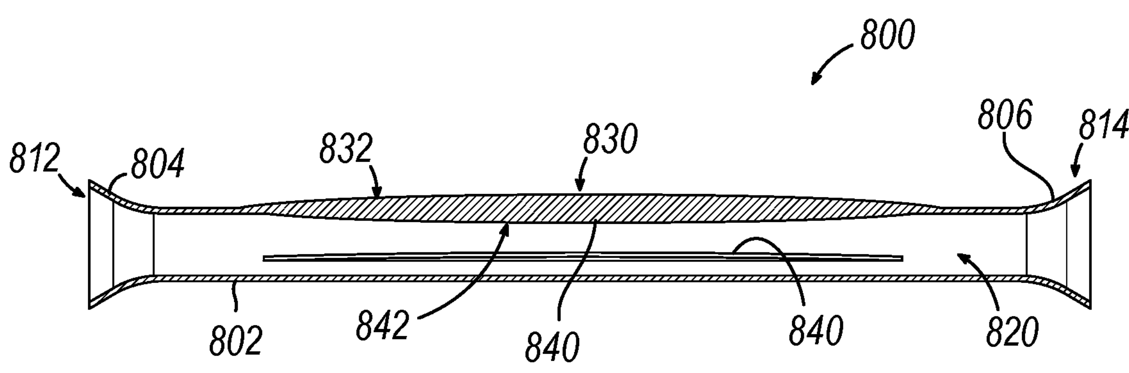
FIG. 24 depicts a cross-sectional view of the insert member of FIG. 22, taken along line 24-24 of FIG. 23.

During use of a catheter assembly (100), some operators may tend to directly grasp catheter (120) near the point at which catheter (120) enters port (250) of guiding sheath (200). In some scenarios, the presence of blood, saline, or other fluids on catheter (120) may make it difficult to grip catheter (120). In addition to facilitating insertion of catheter (120) into port (250) of guiding sheath (200), an insert member may be configured to enhance an operator's grip of catheter (120). This may include enabling an insert member to be used to rotate catheter (120) about the longitudinal axis (LA) of catheter (120). FIGS. 22-24 show an example of an insert member (800) that includes features that many enhance an operator's grip of catheter (120), providing further stability to the operator's grip of catheter (120), and facilitating rotation of catheter (120) about the longitudinal axis (LA) of catheter (120).

Insert member (800) of the present example includes a cylindrical body (802), a flared distal portion (812), and a flared proximal portion (814). Body (802) distally terminates at flared distal portion (812) and proximally terminates at flared proximal portion (814). Distal portion (812) has a frustoconical shape leading into lumen (820) and defines distal end (804) of insert member (800). Proximal portion (814) has a frustoconical shape leading into lumen (820) and defines proximal end (806) of insert member (800). While distal portion (812) is flared in the present example, other versions of insert member (800) may have a straight distal portion (e.g., like insert members (300, 400, 500, 550, 580, 600, 700, 750)). In some versions, the flared configuration of distal portion (812) prevents distal portion (812) from being inserted into insertion port (250) of guiding sheath (200). In some other versions, the flared configuration of distal portion (812) permits distal portion (812) to pass into the opening (254) of annular protrusion (252) of insertion port (250); but prevents distal portion (812) from being inserted through seal (260). In any case, the user of the term "insert member" should not be read as necessarily requiring an "insert member" to be insertable into an insertion port (250) or other structure.

In the present example, insert member (800) is substantially rigid. Insert member (800) further includes a plurality of exterior fins (830) extending longitudinally and radially outwardly from body (802). Exterior fins (830) are equidistantly spaced angularly about the longitudinal axis of insert member (800). While insert member (800) has three exterior fins (830) in the present example, other versions may have more or fewer than three exterior fins (830). As best seen in FIG. 24, each exterior fin (830) has an outer edge (832) that extends along a curve from the proximal end of exterior fin (830) to the distal end of exterior fin (830). Exterior fins (830) may facilitate grasping of insert member (800) by an operator. Exterior fins (830) may also facilitate rotation of insert member (800) about the longitudinal axis of insert member (800) (and thereby facilitate rotation of catheter (120) about the longitudinal axis of catheter (120), as described below) by an operator.

As best seen in FIGS. 23-24, insert member (800) further includes a plurality of interior fins (840) extending longitudinally and radially inwardly in lumen (820). Interior fins (840) are equidistantly spaced angularly about the longitudinal axis of insert member (800). While insert member (800) has three interior fins (840) in the present example, other versions may have more or fewer than three interior fins (840). As best seen in FIG. 24, each interior fin (840) has an edge (842) that extends along a curve from the proximal end of interior fin (840) to the distal end of interior fin (840).

Figure 25:
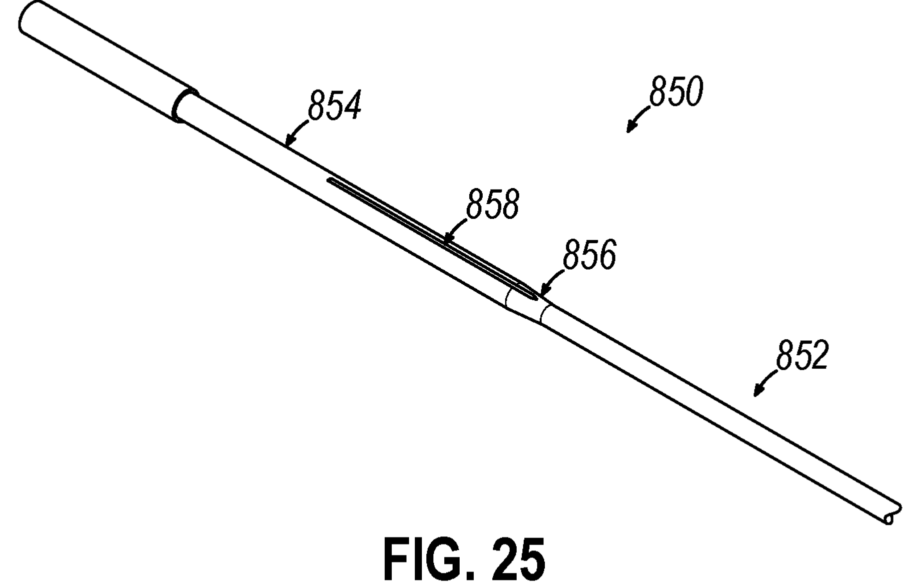
FIG. 25 depicts a perspective view of another example of a catheter that may be incorporated into the catheter assembly of FIG. 1.
Figures 26A, 26B:
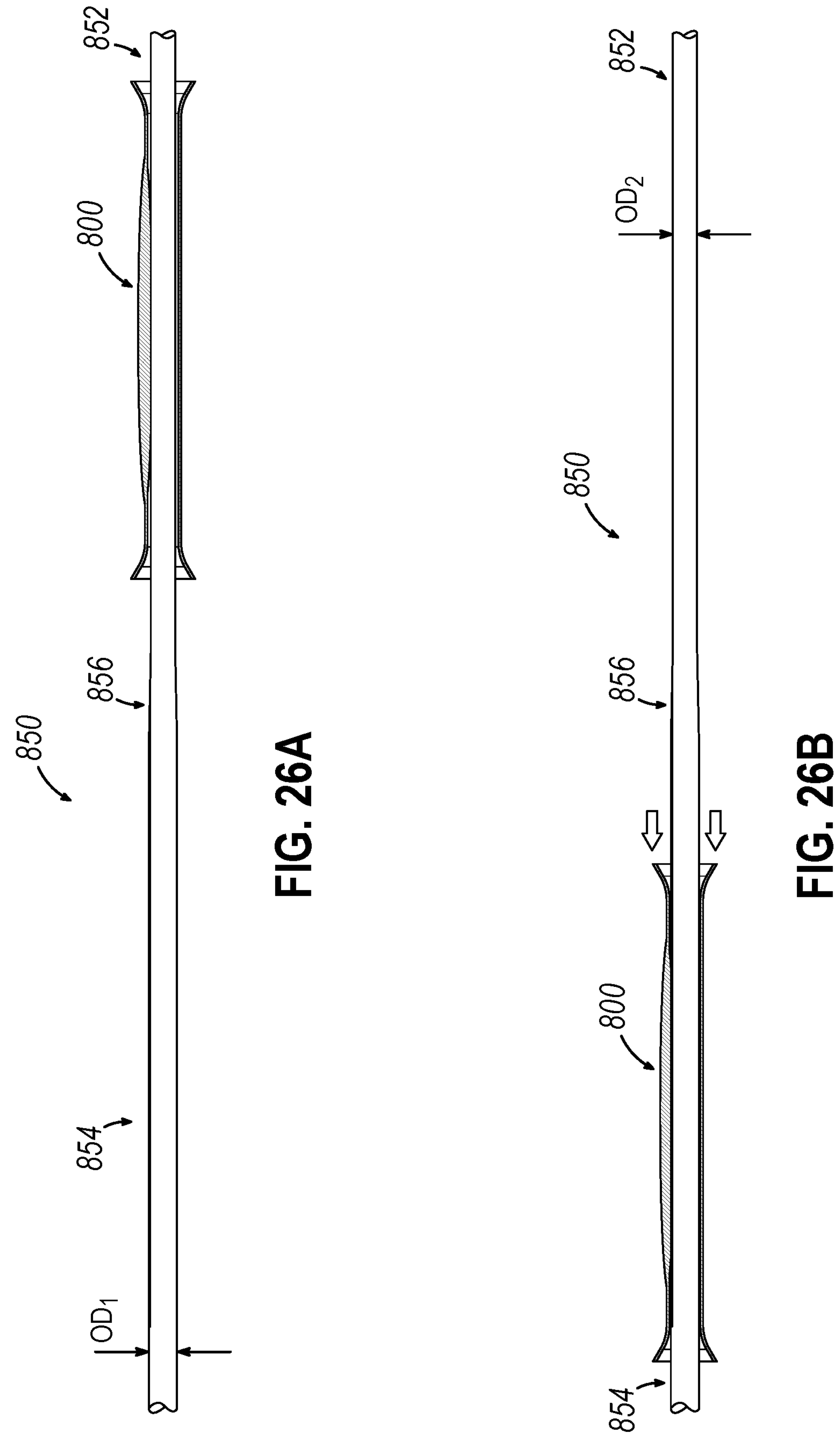
FIG. 26A depicts a cross-sectional side view of the insert member of FIG. 22 positioned about the catheter of FIG. 5, with the insert member in a first longitudinal position along the catheter.
FIG. 26B depicts a cross-sectional side view of the insert member of FIG. 22 positioned about the catheter of FIG. 5, with the insert member in a second longitudinal position along the catheter.

Interior fins (840) are configured to engage the exterior of catheter (120) and substantially (yet removably) secure insert member (800) to catheter (120). Such engagement may be enhanced when catheter (120) is modified to include two different outer diameters. An example of such a modified catheter (850) is shown in FIGS. 25-26B. Catheter (850) may be readily incorporated into catheter assembly (100) in place of catheter (120). In this example, catheter (850) includes a distal portion (852) and a proximal portion (854), with a transitional region (856) between portions (852, 856). As best seen in FIGS. 26A-26B, distal portion (852) has a first outer diameter ($OD_1$); while proximal portion (854) has a second outer diameter ($OD_2$). Second outer diameter ($OD_2$) is larger than first outer diameter (ON. Transitional region (856) provides a tapering transition from first outer diameter ($OD_1$) to second outer diameter ($OD_2$). In the present example, proximal portion (854) further includes a plurality of longitudinally extending recesses (858). Recesses (858) are sized and positioned to correspond with the size and positioning of interior fins (840) of insert member (800). In some other versions, recesses (858) are omitted, as recesses (858) are not necessarily required.

Insert member (800) may be slid along the length of catheter (850) between a distal position (FIG. 26A) and a proximal position (FIG. 26B). First outer diameter ($OD_1$) is sized to be smaller than the effective inner diameter defined by interior fins (840) of insert member (800). Thus, while interior fins (840) may contact the exterior of distal portion (852) of catheter (850) while insert member (800) is in the distal position as shown in FIG. 26A, interior fins (840) will not prevent insert member (800) from sliding freely along distal portion (852) of catheter (850).

When insert member (800) is slid proximally to the proximal position as shown in FIG. 26B, interior fins (840) engage the exterior of proximal portion (854) of catheter (850). In some versions, second outer diameter ($OD_2$) is sized to be larger than the effective inner diameter defined by interior fins (840) of insert member (800). In some such versions, engagement between interior fins (840) and the exterior of proximal portion (854) of catheter (850) provides friction, such that insert member (800) effectively grips onto proximal portion (854) of catheter (850) when insert member is in the proximal position shown in FIG. 26B. In some other versions, interior fins (840) have a higher durometer than catheter (850), such that interior fins (840) dig into or otherwise deform proximal portion (854) of catheter (850) when insert member is in the proximal position shown in FIG. 26B. In some versions, proximal portion (854) of catheter (850) includes an elastomeric coating, elastomeric overmold, or other feature that promotes frictional or deforming engagement with interior fins (840). In either case, the engagement between interior fins (840) and the exterior of proximal portion (854) of catheter (850) may enable insert member (800) to be used as a grasping point for catheter (850), thereby facilitating operator manipulation of catheter (850), including but not limited to rotation of catheter (850) about the longitudinal axis of catheter (850). Nevertheless, the engagement between interior fins (840) and the exterior of proximal portion (854) of catheter (850) may also allow the operator to firmly grasp catheter (850) and insert member (800) simultaneously; and slide insert member (800) distally along catheter (850) back toward the distal position of FIG. 26A, to thereby disengage interior fins (840) from the exterior of proximal portion (854) of catheter (850).

In some versions where catheter (850) includes recesses (858), interior fins (840) do not necessarily provide a frictional or deforming fit with the exterior of proximal portion (854) of catheter (850). In some such versions, interior fins (840) are configured to simply enter recesses (858) and facilitate use of insert member (800) to rotate catheter (850) about the longitudinal axis of catheter (850), with insert member (800) being freely slidably along proximal portion (854) of catheter (850). Alternatively, interior fins (840) may provide a frictional or deforming fit with the exterior of proximal portion (854) of catheter (850) when interior fins (840) are disposed in recesses (858). As noted above, recesses (858) may be omitted in some versions.

VIII. EXAMPLE OF INSERT MEMBER ASSEMBLY WITH SELECTIVE GRIPPING OF CATHETER

As noted above, it may be desirable to provide an insert member that facilitates grasping of catheter (120) and other manipulation (e.g., rotation, etc.) of catheter (120). While insert member (800) described above provides selectively locking engagement between insert member (800) and a proximal portion (854) of catheter (850), it may be desirable to provide selective locking engagement between an insert member and other longitudinal regions of a catheter (120). In other words, it may be desirable to enable an operator to selectively secure an insert member at various positions along the length of catheter (120), beyond just a proximal portion of catheter (120). Such selective positioning and locking may be based on operator preference, the anatomy of the patient at hand, or other factors. FIGS. 27A-30B show an insert member assembly (900) that is capable of such operation.

Insert member assembly (900) of the present example includes a male member (910), a deformable member (950), and a female member (960). As described in greater detail below, deformable member (950) is configured to be captured between portions of male and female members (910, 960); and be selectively compressed to selectively lock insert member assembly against the exterior of a catheter (120).

Male member (910) of the present example includes a cylindrical body (912), a flared portion (916), and a head portion (930). Body (912) terminates in one end (914) at flared portion (916) and in the other end (934) at head portion (930). Head portion (930) has an enlarged diameter relative to body (912) and includes an exterior threading (930). Male member (910) defines a lumen (920) that is sized to receive catheter (120), with flared portion (916) providing a lead-in to lumen (920) in scenarios where catheter (120) is initially inserted into insert member assembly (900) via male member (910).

Deformable member (950) of the present example includes a cylindrical body (952) defining a lumen (954). Deformable member (950) is positioned to abut end (934) of male member (910) when insert member assembly (900) is fully assembled. Deformable member (950) is formed of a biocompatible elastomeric deformable material in this example. By way of example only, deformable member (950) may be formed of silicone. Other suitable materials that may be used to form deformable member (950) will be apparent to those skilled in the art in view of the teachings herein.

Figure 29:
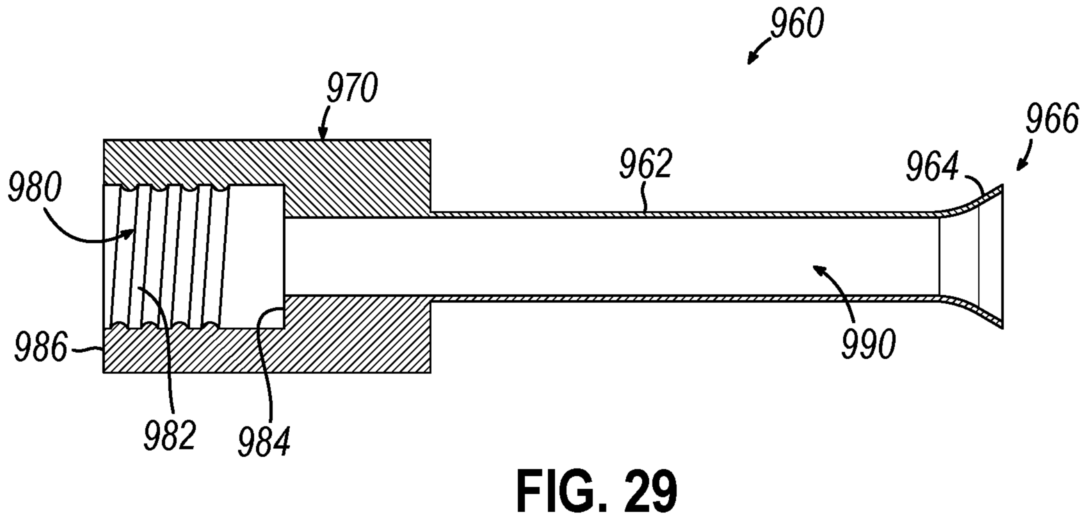
FIG. 29 depicts a cross-sectional side view of a female member of the insert assembly of FIG. 27A.

Female member (950) of the present example includes a cylindrical body (962), a flared portion (966), and a head portion (970). Body (962) terminates in one end (964) at flared portion (966) and in the other end (986) at head portion (970). As best seen in FIG. 29, head portion (970) has an enlarged diameter relative to body (962) and includes a recess (980) having an interior threading (982) and an interior boss surface (984). Interior threading (982) of female member (960) complements exterior threading (932) of male member (910). Female member (950) defines a lumen (990) that is sized to receive catheter (120), with flared portion (966) providing a lead-in to lumen (990) in scenarios where catheter (120) is initially inserted into insert member assembly (900) via female member (950).

Figure 27A:
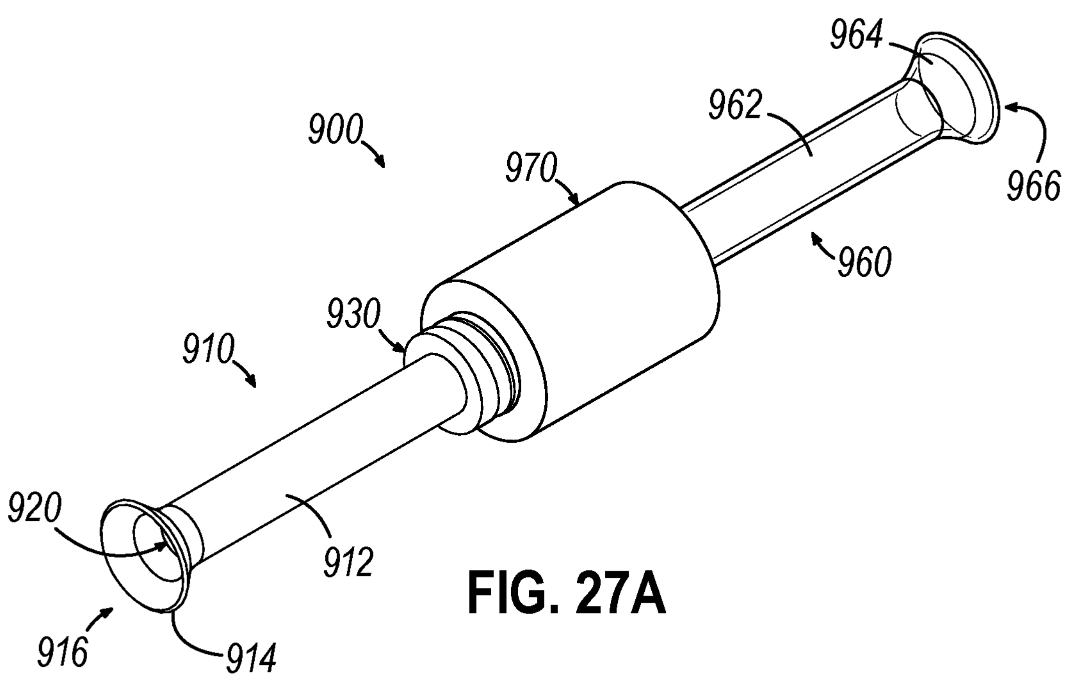
FIG. 27A depicts a perspective view of an example of an insert assembly that may be used with the catheter assembly of FIG. 1 and the guiding sheath of FIG. 4, with the insert assembly in a non-gripping state.
Figure 30A:
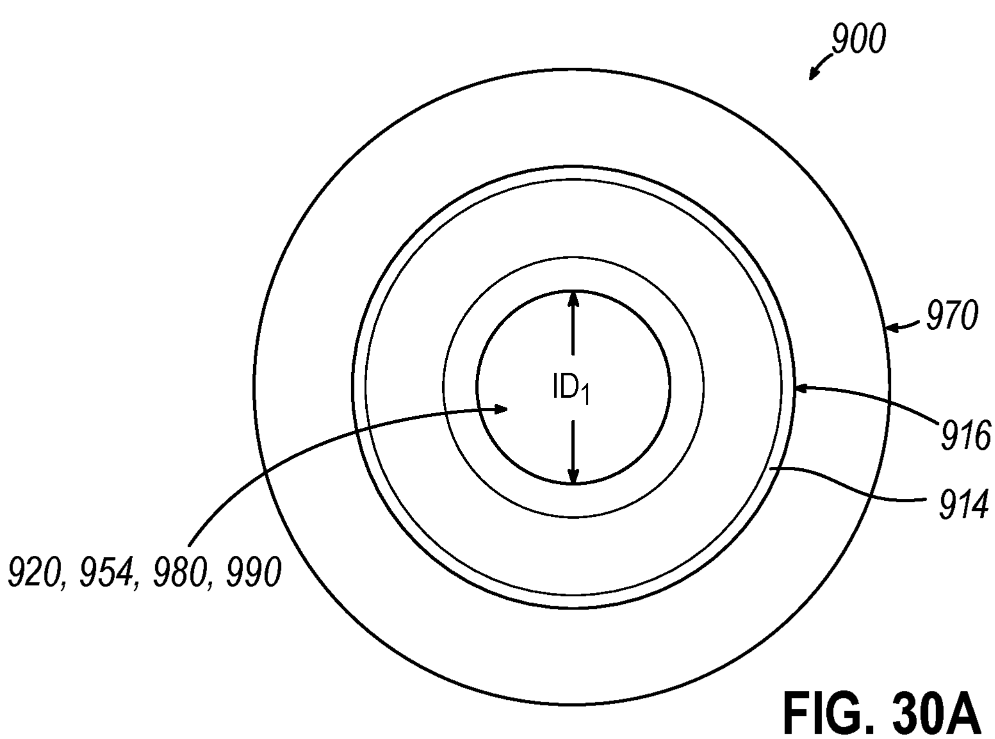
FIG. 30A depicts an end view of the insert assembly of FIG. 27A, with the insert assembly in the non-gripping state.

When insert assembly (900) is in a fully assembled state, deformable member (950) is positioned in recess (980) and is longitudinally captured between end (934) of male member (910) and interior boss surface (984) of female member (950). Threading (932) of male member (910) is received in threading (932) of female member (960). Lumens (920, 954, 990) are longitudinally aligned with each other. With insert assembly (900) fully assembled, catheter (120) may be inserted into lumens (920, 954, 99). With insert assembly (900) in an unlocked state as shown in FIGS. 27A and 30A, female member (950) is in a substantially relaxed state, such that lumen (954) defines a first inner diameter ($ID_1$) that is at least as large as the outer diameter of catheter (120). Insert assembly (900) may thus slide freely along the exterior of catheter (120) when insert assembly (900) is in the unlocked state as shown in FIGS. 27A and 30A.

Figure 27B:
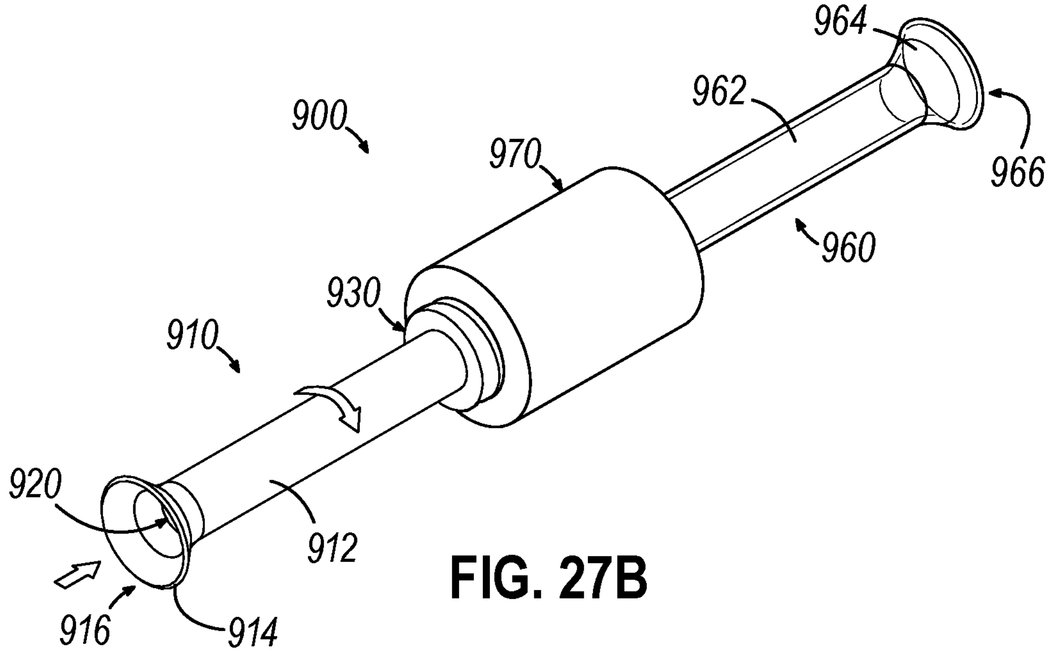
FIG. 27B depicts a perspective view of the insert assembly of FIG. 27A, with the insert assembly in a gripping state.
Figure 28:
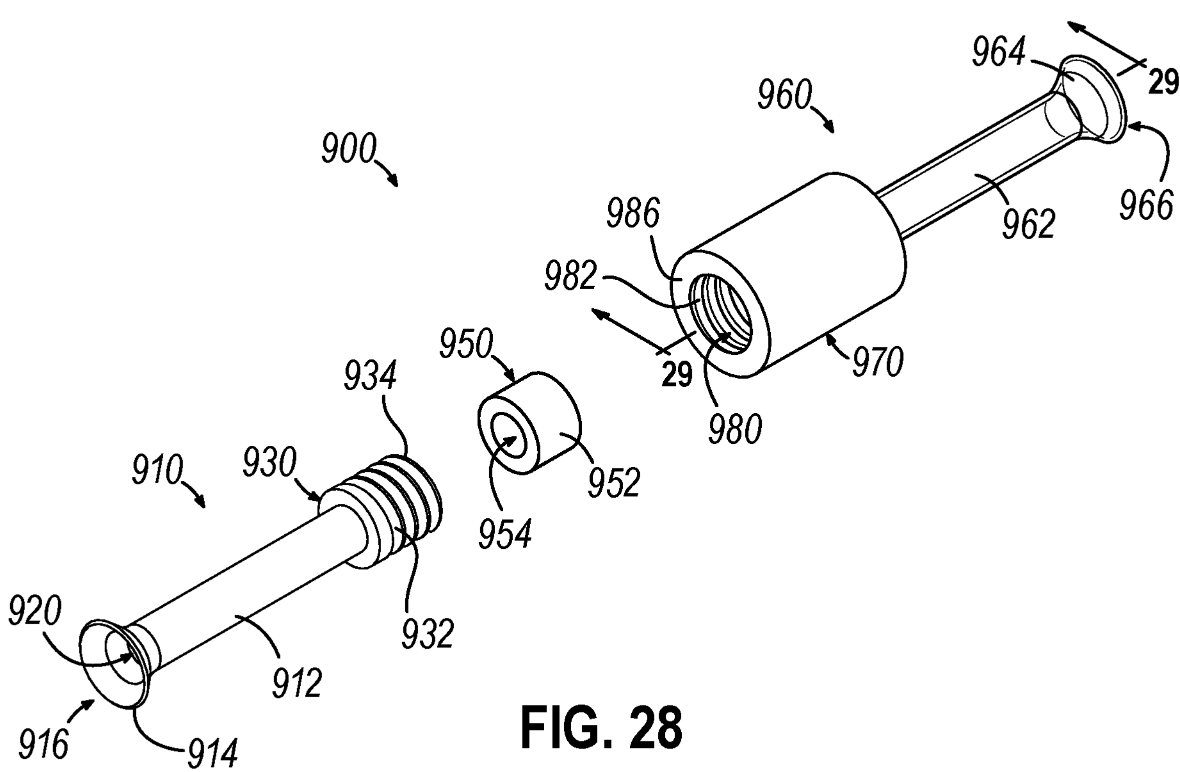
FIG. 28 depicts an exploded perspective view of the insert assembly of FIG. 27A.
Figure 30B:
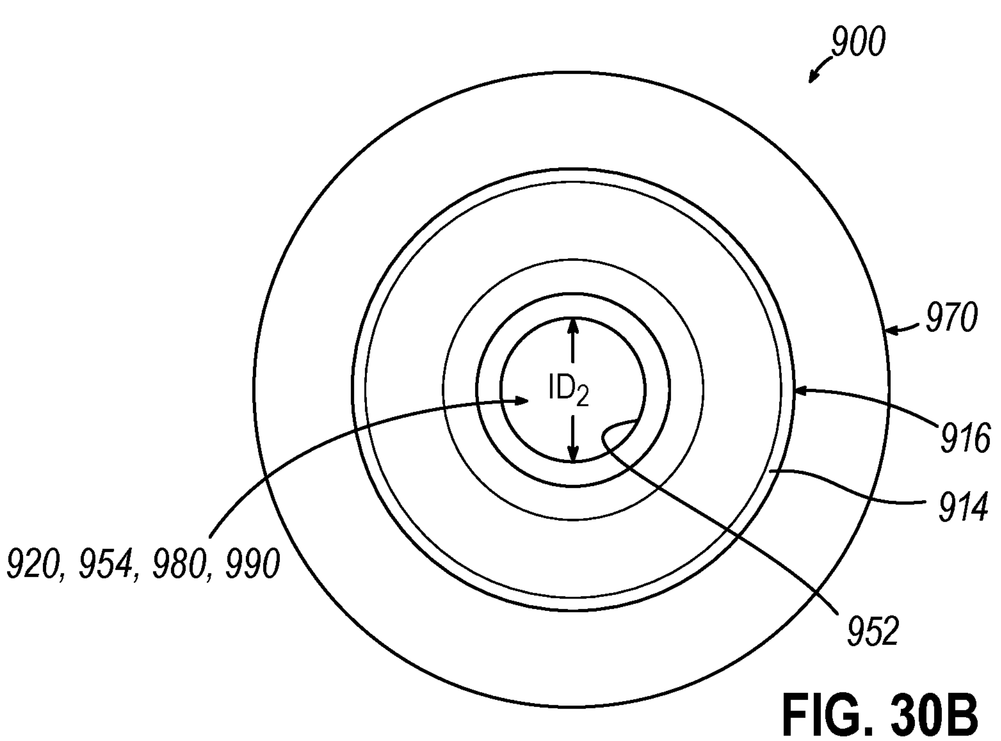
FIG. 30B depicts an end view of the insert assembly of FIG. 27A, with the insert assembly in the gripping state.

When the operator wishes to lock the position of insert assembly (900) at a selected longitudinal position along the length of catheter (120), the operator may rotate male member (910) relative to female member (950); or rotate female member (950) relative to male member (910). Such relative rotation may transition insert assembly to a locked state as shown in FIGS. 27B and 30B. In the transition from the unlocked state of FIGS. 27A and 30A to the locked state of FIGS. 27B and 30B, the engagement between threading (932) of male member (910) and threading (932) of female member (960) provides translation of male member (910) toward female member (960), which in turn provides longitudinal compression of deformable member (950) between end (934) of male member (910) and interior boss surface (984) of female member (950). This longitudinal compression of deformable member (950) causes deformable member (950) to deform inwardly, which in turn reduces the inner diameter ($ID_2$) of lumen (954). In this state, the inner diameter ($ID_2$) of lumen (954) is smaller than the outer diameter of catheter (120), such that deformable member (950) bears inwardly against catheter (120). This results in insert assembly (900) frictionally gripping catheter (120).

With insert assembly (900) frictionally gripping catheter (120) in the locked state shown in FIGS. 27A and 30B, the operator may grasp insert assembly (900) to further manipulate catheter (120) (e.g., translate catheter, rotate catheter (120) about the longitudinal axis of catheter (120), etc.). Insert assembly (900) may further include fins, ridges, knurling, or other features to promote gripping between the operator's hands and insert assembly (900).

While ends (914, 964) of insert assembly (900) are both flared in the present example, some versions of insert assembly (900) may lack flared portion (916) or flared portion (966). For instance, male member (910) may lack flared portion (916) in scenarios where it is desirable to insert end (914) through seal (260) of insertion port (250). Similarly, female member (960) may lack flared portion (966) in scenarios where it is desirable to insert end (964) through seal (260) of insertion port (250). In versions where either end (914, 964) is insertable through seal (260) of insertion port (250), the compressed deformable member (950) may form a fluid-tight seal against catheter (120), such that deformable member (950) may function similar to the various seal members (406, 530, 560, 590, 630) described herein.

In versions where ends (914, 964) of insert assembly (900) are both flared as shown in FIGS. 27A-30B, the flared configuration of ends (914, 964) may prevents either end (914, 964) from being inserted into insertion port (250) of guiding sheath (200). In some other versions, the flared configuration of ends (914, 964) permits either end (914, 964) to pass into the opening (254) of annular protrusion (252) of insertion port (250); but prevents either end (914, 964) from being inserted through seal (260).

IX. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a cylindrical shaft, the cylindrical shaft being sized for insertion into an insertion port of a cardiovascular catheter guiding sheath, the cylindrical shaft including: (i) a proximal end, (ii) a distal end, and (iv) a lumen extending from the proximal end to the distal end, the lumen being sized to receive an end effector and catheter of a cardiovascular catheter instrument; and (b) an outwardly flared feature at the proximal end of the cylindrical shaft, the outwardly flared feature defining an angled surface leading into the lumen.

Example 2

The apparatus of Example 1, the cylindrical shaft and the outwardly flared feature including a rigid material.

Example 3

The apparatus of any one or more of Examples 1 through 2, further comprising a seal member disposed in the lumen, the seal member being configured to form a fluid tight seal against a catheter disposed in the lumen.

Example 4

The apparatus of Example 3, the seal member including an elastomeric material.

Example 5

The apparatus of any one or more of Examples 3 through 4, the seal member being positioned at an intermediate location along the cylindrical shaft, between the proximal end and the distal end.

Example 6

The apparatus of any one or more of Examples 3 through 5, the seal member including one or more outwardly extending tabs, the one or more outwardly extending tabs being configured to secure the position of the seal member in the lumen.

Example 7

The apparatus of Example 6, the cylindrical shaft defining one or more apertures configured to receive the one or more outwardly extending tabs.

Example 8

The apparatus of any one or more of Examples 3 through 7, the seal member including a pair of ramped internal surfaces that converge at a ridge, the ridge being configured to engage a catheter disposed in the seal member.

Example 9

The apparatus of any one or more of Examples 1 through 8, further comprising a catheter disposed in the lumen, the catheter being configured to fit within a cardiovascular anatomical structure.

Example 10

The apparatus of Example 9, the catheter including a distal end with an end effector.

Example 11

The apparatus of Example 10, the end effector including at least one mapping electrode configured to pick up potentials from tissue.

Example 12

The apparatus of any one or more of Examples 10 through 11, the end effector including at least one ablation electrode configured to ablate tissue.

Example 13

The apparatus of any one or more of Examples 1 through 12, further comprising a cardiovascular catheter guiding sheath having an insertion port configured to receive the cylindrical shaft.

Example 14

The apparatus of Example 13, the insertion port defining an opening with a seal positioned in the opening.

Example 15

The apparatus of Example 14, the cylindrical shaft being configured to pass through the seal.

Example 16

The apparatus of Example 15, the seal including a slit configuration configured to permit the shaft to pass through the seal.

Example 17

The apparatus of any one or more of Examples 13 through 16, the insertion port and the outwardly flared feature being configured to prevent the outwardly flared feature from passing through the insertion port.

Example 18

The apparatus of any one or more of Examples 1 through 17, the outwardly flared feature having a frustoconical shape.

Example 19

A kit, comprising: (a) a catheter instrument including: (i) a catheter having a distal end, and (ii) an end effector at the distal end of the catheter, the catheter and the end effector being sized to fit in a cardiovascular anatomical structure; and (b) an insert member including: (i) a cylindrical shaft including: (A) a proximal end, (B) a distal end, and (C) a lumen extending from the proximal end to the distal end, the lumen being sized to receive the end effector and the catheter, and (ii) an outwardly flared feature at the proximal end of the cylindrical shaft, the outwardly flared feature defining an angled surface leading into the lumen.

Example 20

The kit of Example 19, the end effector including at least one electrode.

Example 21

The kit of any one or more of Examples 19 through 20, further comprising a cardiovascular catheter guiding sheath, the cardiovascular catheter guiding sheath including an insertion port configured to receive the cylindrical shaft and the catheter.

Example 22

The kit of Example 21, the outwardly flared feature being configured to arrest insertion of the insert member into the insertion port.

Example 23

The kit of any one or more of Examples 21 through 22, the outwardly flared feature being configured to arrest insertion of the catheter into the insertion port.

Example 24

A method comprising: positioning an insert member on a catheter, the insert member including: (i) a cylindrical shaft including: (A) a proximal end, (B) a distal end, and (C) a lumen extending from the proximal end to the distal end, the lumen receiving the catheter, and (ii) an outwardly flared feature at the proximal end of the cylindrical shaft, the outwardly flared feature defining an angled surface leading into the lumen; the catheter being sized for insertion into a cardiovascular anatomical structure.

Example 25

The method of Example 24, further comprising passing the distal end of the cylindrical shaft through an insertion port of a cardiovascular catheter guiding sheath.

Example 26

The method of Example 25, the step of positioning the insert member on the catheter being performed before the step of passing the distal end of the cylindrical shaft through the insertion port of the cardiovascular catheter guiding sheath.

Example 27

The method of any one or more of Examples 25 through 26, the catheter having a distal end with an end effector, the end effector being positioned between the proximal end of the cylindrical shaft and the distal end of the cylindrical shaft during the step of passing the distal end of the cylindrical shaft through the insertion port of the cardiovascular catheter guiding sheath.

Example 28

The method of any one or more of Examples 25 through 27, further comprising advancing the catheter distally relative to the insert member and relative to the cardiovascular catheter guiding sheath after performing the step of passing the distal end of the cylindrical shaft through the insertion port of the cardiovascular catheter guiding sheath.

Example 29

The method of Example 28, further comprising engaging the outwardly flared feature with the insertion port of the cardiovascular catheter guiding sheath, the engaged outwardly flared feature arresting distal movement of the insert member relative to the insertion port.

Example 30

The method of Example 29, further comprising engaging a portion of a handle assembly at a proximal end of the catheter with the outwardly flared feature, the outwardly flared feature arresting distal movement of the catheter via engagement with the portion of the handle assembly.

Example 31

The method of any one or more of Examples 24 through 30, the insert member further including a seal in the lumen, the seal forming a fluid tight seal against an outer surface of the catheter.

Example 32

The method of Example 31, the seal deforming elastically to form the fluid tight seal against the outer surface of the catheter.

Example 33

The method of any one or more of Examples 24 through 32, further comprising positioning a distal portion of the catheter in a cardiovascular anatomical structure of a patient.

Example 34

The apparatus of any one or more of Examples 3 through 7, the seal member including an inner surface having a bell curve shaped cross-sectional profile.

Example 35

The apparatus of any one or more of Examples 3 through 7, the seal member including an inner surface having an arcuate cross-sectional profile.

Example 36

The apparatus of any one or more of Examples 3 through 7, the seal member having a corrugated configuration.

Example 37

The apparatus of any one or more of Examples 1 through 36, further including a plurality of ribs extending outwardly from the cylindrical shaft.

Example 38

The apparatus of Example 37, the ribs extending longitudinally along the cylindrical shaft, the ribs being angularly spaced apart from each other about the cylindrical shaft.

Example 39

The apparatus of any one or more of Examples 37 through 38, the ribs extending circumferentially about the cylindrical shaft, the ribs being longitudinally spaced apart from each other along the cylindrical shaft.

Example 40

The apparatus of any one or more of Examples 1 through 39, further comprising a plurality of exterior fins extending outwardly from the cylindrical shaft, the exterior fins extending longitudinally along the cylindrical shaft, the exterior fins being angularly spaced apart from each other about the cylindrical shaft.

Example 41

The apparatus of any one or more of Examples 1 through 39, further comprising a plurality of interior fins extending inwardly within the lumen of the cylindrical shaft, the interior fins extending longitudinally along the lumen of the cylindrical shaft, the interior fins being angularly spaced apart from each other about the lumen of the cylindrical shaft.

Example 42

The apparatus of Example 41, further comprising a catheter disposed in the lumen, the catheter being configured to fit within a cardiovascular anatomical structure, the catheter having a first longitudinal region having a first outer diameter and a second longitudinal region having a second outer diameter, the interior fins being configured to permit the cylindrical shaft to slide along the first longitudinal region of the catheter, the interior fins being configured to resist sliding of the cylindrical shaft along the second longitudinal region of the catheter.

Example 43

The apparatus of any one or more of Examples 1 through 42, further comprising an outwardly flared feature at the distal end of the cylindrical shaft, the outwardly flared feature defining an angled surface leading into the lumen.

Example 44

The apparatus of any one or more of Examples 1 through 43, the cylindrical shaft including a first segment and a second segment, the first segment having a male engagement portion, the second segment having a female engagement portion, the apparatus further comprising a deformable member captured between the male engagement portion and the female engagement portion, the first and second segments being movable relative to each other to thereby deform the deformable member, the deformable member in a deformed state being configured to secure a position of the cylindrical shaft to a catheter, the deformable member in a non-deformed state being configured to allow the cylindrical shaft to slide along the catheter.

X. MISCELLANEOUS

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a cylindrical shaft, the cylindrical shaft being sized for insertion into an insertion port of a cardiovascular catheter guiding sheath, the cylindrical shaft including:

(i) a proximal end, (ii) a distal end, (iii) a lumen extending from the proximal end to the distal end, the lumen being sized to receive an end effector and a catheter of a cardiovascular catheter instrument, and (iv) a deformable seal member secured within the lumen, the deformable seal member comprising a material having a lower durometer than a durometer of the cylindrical shaft, the deformable seal member configured to deform against an outer surface of the end effector or catheter when the end effector and catheter are inserted through the cylindrical shaft to thereby form a fluid tight seal against the end effector or catheter while also allowing the catheter to translate through the lumen of the cylindrical shaft, the deformable seal member comprising one or more coupling portions that extend into one or more openings through a sidewall of the cylindrical shaft such that the one or more coupling portions comprise an exposed outer surface; and (b) an outwardly flared feature at the proximal end of the cylindrical shaft, the outwardly flared feature defining an angled surface leading into the lumen.

2. The apparatus of claim 1, the cylindrical shaft and the outwardly flared feature including a rigid material.

3. The apparatus of claim 1, the deformable seal member including a pair of ramped internal surfaces that converge at a ridge, the ridge being configured to deform against the outer surface of the end effector or catheter when the end effector and catheter are inserted through the cylindrical shaft.

4. The apparatus of claim 1, the deformable seal member including an inner surface having a bell curve shaped cross-sectional profile.

5. The apparatus of claim 1, the deformable seal member including an inner surface having an arcuate cross-sectional profile.

6. The apparatus of claim 1, further including a plurality of ribs extending outwardly from the cylindrical shaft.

7. The apparatus of claim 6, the plurality of ribs extending longitudinally along the cylindrical shaft, the plurality of ribs being angularly spaced apart from each other about the cylindrical shaft.

8. The apparatus of claim 6, the plurality of ribs extending circumferentially about the cylindrical shaft, the plurality of ribs being longitudinally spaced apart from each other along the cylindrical shaft.

9. The apparatus of claim 1, further comprising a plurality of exterior fins extending outwardly from the cylindrical shaft, the plurality of exterior fins extending longitudinally along the cylindrical shaft, the plurality of exterior fins being angularly spaced apart from each other about the cylindrical shaft.

10. The apparatus of claim 1, further comprising a plurality of interior fins extending inwardly within the lumen of the cylindrical shaft, the plurality of interior fins extending longitudinally along the lumen of the cylindrical shaft, the plurality of interior fins being angularly spaced apart from each other about the lumen of the cylindrical shaft.

11. The apparatus of claim 10, further comprising a catheter disposed in the lumen, the catheter being configured to fit within a cardiovascular anatomical structure, the catheter having a first longitudinal region having a first outer diameter and a second longitudinal region having a second outer diameter, the plurality of interior fins being configured to permit the cylindrical shaft to slide along the first longitudinal region of the catheter, the plurality of interior fins being configured to resist sliding of the cylindrical shaft along the second longitudinal region of the catheter.

12. The apparatus of claim 1, further comprising an outwardly flared feature at the distal end of the cylindrical shaft, the outwardly flared feature defining an angled surface leading into the lumen.

13. The apparatus of claim 1, further comprising the catheter disposed in the lumen, the catheter being configured to fit within a cardiovascular anatomical structure.

14. The apparatus of claim 1, further comprising the cardiovascular catheter guiding sheath having an insertion port configured to receive the cylindrical shaft, the insertion port defining an opening with a port seal positioned in the opening, the cylindrical shaft being configured to pass through the port seal, the insertion port and the outwardly flared feature being configured to prevent the outwardly flared feature from passing through the insertion port.

15. A kit, comprising:

(a) a catheter instrument including:

(i) a catheter having a distal end, and (ii) an end effector at the distal end of the catheter, the catheter and the end effector being sized to fit in a cardiovascular anatomical structure, the end effector including at least one electrode; and (b) an insert member including:

(i) a cylindrical shaft including:

(A) a proximal end, (B) a distal end, (C) a lumen extending from the proximal end of the cylindrical shaft to the distal end of the cylindrical shaft, the lumen being sized to receive the end effector and the catheter, and (D) a deformable seal member secured within the lumen, the deformable seal member comprising a material having a lower durometer material than a durometer of the cylindrical shaft, the deformable seal configured to deform against an outer surface of the catheter instrument when the catheter instrument is inserted through the cylindrical shaft to thereby form a fluid tight seal against the catheter instrument while also allowing the catheter instrument to translate through the lumen of the cylindrical shaft, the deformable seal member comprising one or more coupling portions that extend into one or more openings through a sidewall of the cylindrical shaft such that the one or more coupling portions comprise an exposed outer surface; and (ii) an outwardly flared feature at the proximal end of the cylindrical shaft, the outwardly flared feature defining an angled surface leading into the lumen.

16. The kit of claim 15, further comprising a cardiovascular catheter guiding sheath, the cardiovascular catheter guiding sheath including an insertion port configured to receive the cylindrical shaft and the catheter instrument.

17. A method comprising:

positioning an insert member on a catheter, the insert member including:

(i) a cylindrical shaft including:

(A) a proximal end, (B) a distal end, (C) a lumen extending from the proximal end to the distal end, the lumen receiving the catheter, and (D) a deformable seal member secured within the lumen, the deformable seal member comprising a material having a lower durometer than a durometer of the cylindrical shaft, the deformable seal member configured to deform against an outer surface of the catheter when the catheter is inserted through the cylindrical shaft to thereby form a fluid tight seal against the catheter while also allowing the catheter to translate through the lumen of the cylindrical shaft, the deformable seal member comprising one or more coupling portions that extend into one or more openings through a sidewall of the cylindrical shaft such that the one or more coupling portions comprise an exposed outer surface; and (ii) an outwardly flared feature at the proximal end of the cylindrical shaft, the outwardly flared feature defining an angled surface leading into the lumen;

the catheter being sized for insertion into a cardiovascular anatomical structure.

* * * * *